United States Patent
Gee et al.

(10) Patent No.: US 10,570,250 B2
(45) Date of Patent: Feb. 25, 2020

(54) DIBENZOSILOLE MONOMERS AND POLYMERS AND METHODS FOR THEIR PREPARATION AND USE

(71) Applicant: LIFE TECHNOLOGIES CORPORATION, Carlsbad, CA (US)

(72) Inventors: Kyle Gee, Springfield, OR (US); Xin Wang, Eugene, OR (US); Hee Chol Kang, Eugene, OR (US); Aimei Chen, Eugene, OR (US); Yexin Wu, Eugene, OR (US); Yi-Zhen Hu, Eugene, OR (US); Robert Aggeler, Eugene, OR (US); Quentin Low, Eugene, OR (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 0 days.

(21) Appl. No.: 16/107,818

(22) Filed: Aug. 21, 2018

(65) Prior Publication Data

US 2018/0355098 A1 Dec. 13, 2018

Related U.S. Application Data

(63) Continuation of application No. 15/491,650, filed as application No. PCT/US2015/045351 on Aug. 14, 2015, now Pat. No. 10,087,280.

(60) Provisional application No. 62/074,368, filed on Nov. 3, 2014.

(51) Int. Cl.

| | |
|---|---|
| C08G 61/12 | (2006.01) |
| H01L 51/00 | (2006.01) |
| C07F 7/08 | (2006.01) |
| C08L 65/00 | (2006.01) |
| G01N 33/533 | (2006.01) |
| G01N 33/58 | (2006.01) |
| C09K 11/06 | (2006.01) |
| G01N 33/545 | (2006.01) |

(52) U.S. Cl.
CPC .......... *C08G 61/123* (2013.01); *C07F 7/083* (2013.01); *C07F 7/0816* (2013.01); *C08L 65/00* (2013.01); *C09K 11/06* (2013.01); *G01N 33/533* (2013.01); *G01N 33/545* (2013.01); *G01N 33/582* (2013.01); *H01L 51/0039* (2013.01); *H01L 51/0043* (2013.01); *H01L 51/0094* (2013.01); *C08G 2261/122* (2013.01); *C08G 2261/124* (2013.01); *C08G 2261/145* (2013.01); *C08G 2261/1424* (2013.01); *C08G 2261/1644* (2013.01); *C08G 2261/1646* (2013.01); *C08G 2261/3142* (2013.01); *C08G 2261/3244* (2013.01); *C08G 2261/334* (2013.01); *C08G 2261/344* (2013.01); *C08G 2261/411* (2013.01); *C08G 2261/522* (2013.01); *C08G 2261/5222* (2013.01); *C08G 2261/72* (2013.01); *C08G 2261/94* (2013.01); *C09K 2211/1416* (2013.01); *C09K 2211/1491* (2013.01)

(58) Field of Classification Search
CPC .................................................... C08G 61/123
See application file for complete search history.

(56) References Cited

U.S. PATENT DOCUMENTS

| | | | |
|---|---|---|---|
| 8,158,444 B2 | 4/2012 | Gaylord et al. | |
| 2003/0168656 A1* | 9/2003 | Kobayashi | C07D 333/76 257/40 |
| 2007/0248839 A1* | 10/2007 | Towns | C08G 61/123 428/690 |
| 2008/0293164 A1 | 11/2008 | Gaylord et al. | |
| 2016/0169920 A1 | 6/2016 | Fukushima et al. | |

FOREIGN PATENT DOCUMENTS

| | | |
|---|---|---|
| WO | WO-2005047363 A1 | 5/2005 |
| WO | WO-2006074471 A2 | 7/2006 |
| WO | WO-2009051560 A1 | 4/2009 |
| WO | WO-2012087243 A1 | 6/2012 |
| WO | WO-2013065573 A1 | 5/2013 |

\* cited by examiner

*Primary Examiner* — Margaret G Moore

(57) ABSTRACT

Water-soluble, conjugated polymers containing one or more dibenzosilole monomer residues, as well as compositions, kits, and methods of making and using such polymers are disclosed. Also disclosed are dibenzosilole derivatives substituted with one or more water-solubilizing groups, and methods of making and using such derivatives to prepare water-soluble dibenzosilole polymers.

9 Claims, 17 Drawing Sheets

| Compound | Ab $\lambda_{max}$ (nm) | Em $\lambda_{max}$ (nm) | QY | Extinction Coefficient (x $10^6$ cm$^{-1}$ M$^{-1}$) |
|---|---|---|---|---|
| Pacific Blue™ | 403 | 455 | 0.78 | 0.046 |
| Alexa Fluor® 405 | 401 | 421 | 0.52 | 0.035 |
| 13 | 388 | 432 | 0.44 | 1.2 |
| 14 | 388 | 431 | N/A | N/A |
| 15 | 386 | 430 | N/A | N/A |
| 16 | N/A | N/A | N/A | N/A |
| 17 | 385 | 430 | 0.37 | 1.2 |
| 18 | 385 | 430 | 0.39 | 1.2 |
| 19 | N/A | N/A | N/A | N/A |
| 20 | 385 | 430 | 0.41 | 1.2 |
| 21 | 385 | 430 | 0.37 | 1.2 |
| 22 | 386 | 431 | 0.42 | 1.3 |
| 23 | 385 | 427 | 0.43 | 1.0 |
| 24 | 390 | 425 | 0.27 | 1.1 |
| 25 | 400 | 421 | 0.42 | 1.1 |
| 26 | 400 | 421 | 0.67 | 2.1 |
| 27 | 380 | 421 | 0.40 | 1.1 |
| 28 | 385 | 421 | 0.66 | 0.8 |
| 29 | 385 | 421 | 0.65 | 0.8 |

FIG. 10

DIBENZOSILOLE MONOMERS AND POLYMERS AND METHODS FOR THEIR PREPARATION AND USE

CROSS-REFERENCE TO RELATED APPLICATIONS

This application is a continuation of U.S. application Ser. No. 15/491,650 filed Apr. 19, 2017, and now U.S. Pat. No. 10,087,280, which is a 371 of International Application No. PCT/US2015/045351 filed Aug. 14, 2015, and claims the benefit of priority to U.S. Provisional Application No. 62/074,368 filed Nov. 3, 2014, the entire contents of which are incorporated herein by reference.

FIELD OF THE INVENTION

Water-soluble dibenzosilole compounds and polymers containing dibenzosilole monomer residues, including methods for their preparation and use.

BACKGROUND OF THE INVENTION

Conjugated dibenzosilole polymers are an important class of materials that can conduct charge and exhibit photoluminescence with high quantum efficiency. In addition to their electroluminescent properties, dibenzosilole polymers are resistant to oxidative degradation and aggregation, even after exposure to high temperature conditions. This combination of favorable physical, chemical and electro-optical properties makes dibenzosilole polymers particularly useful in the fabrication of electronic and photovoltaic devices.

The manufacture of optoelectronic devices is typically conducted in organic solvents (e.g., aromatic hydrocarbons). To improve the solubility in solvents such as xylene, hydrophobic solubilizing groups are typically attached to dibenzosilole polymers. The absence of viable synthetic approaches for preparing water-soluble dibenzosilole derivatives, however, has precluded the use of these materials in applications requiring solubility in aqueous systems. Thus, there exists a need for bright, thermally and optically stable, conjugated polymers that are soluble in aqueous media and exhibit favorable optical properties (e.g., high extinction coefficient and quantum yield), even under intense irradiation.

SUMMARY OF THE INVENTION

Provided herein are novel dibenzosilole monomers and polymers, compositions, kits, and methods for preparing and using these compounds and compositions. The dibenzosilole monomers and polymers described herein include one or more water-solubilizing groups. These water-solubilizing groups can render the monomers and polymers soluble in aqueous environments (e.g., water or buffer). Water-soluble, dibenzosilole polymers are ideally suited for use in various types of biological applications. Dibenzosilole polymers provided herein emit bright, visible light upon UV excitation (e.g., resulting from irradiation with a violet laser) and can exhibit high extinction coefficients and quantum efficiency (e.g., quantum yield >50%).

Water-soluble dibenzosilole-based conjugated polymers provided herein can exhibit extraordinary brightness and possess several advantages over poly(fluorene)s, such as enhanced stability and electronic effects from the silicon moiety. For example, polymers that include one or more dibenzosilole groups within the polymer backbone are photostable and do not dim significantly when dissolved in an aqueous medium (e.g., deionized water, borate buffer, carbonate buffer, or phosphate buffer). The presence of a dibenzosilole group within the polymer backbone provides materials that can resist oxidative degradation or aggregation after exposure to elevated temperatures. In addition to thermal stability, dibenzosilole polymers also exhibit minimal shifts in emission peak that can result from high intensity and/or prolonged irradiation, making them particularly suitable for use in biological applications (e.g., cell imaging and flow cytometry). Further, the rich synthetic chemistry associated with silicon-containing molecules permits a variety of synthetic substitutions of dibenzolsilole monomers and polymers that are not available for fluorinated carbon analogues of such monomers and polymers.

In one aspect, a polymer is provided including a backbone formed from a plurality of linked monomer residues, wherein at least one of the monomer residues comprises a dibenzosilole group and at least one monomer residue is substituted with one or more first water-solubilizing groups. At least one of the monomer residues can include a dibenzosilole group that is substituted with the one or more first water-solubilizing groups.

The backbone of polymers disclosed herein can include a plurality of monomer residues, each comprising a dibenzosilole group substituted with one or more first water-solubilizing groups. The polymer backbone can include a conjugated segment. The polymer backbone can further include at least one monomer residue that comprises an optionally substituted aromatic group that is different from the dibenzosilole group. For example, the aromatic group can be an aryl or heteroaryl group, such as, for example, an aromatic group derived from a phenylene, naphthalene, fluorene, thiophene, carbazole, pyridine, pyrimidine, spirofluorene, indenofluorene, thienopyrazine, dithienosilole, quinoxaline, benzothiadiazole, thienobenzothiophene, thienothiophene, or triarylamine compound. The aromatic group can be substituted with the one or more second water-solubilizing groups, wherein the first and second water-solubilizing groups are the same or different. The water-solubilizing groups can be, for example, alkylene oxide (e.g., ethylene glycol) oligomers or polymers, sulfonate, thiosulfate, phosphonate, boronate, ammonium, alkylammonium (including mono-, bis-, and trialkyl) carboxylate and salts thereof.

Polymers provided herein can exhibit one or more of the following properties or characteristics: fluorescence emission upon excitation at an appropriate wavelength of light (e.g., below about 500 nm); emission of light having a wavelength of greater than about 400 nm; an extinction coefficient of greater than about $2 \times 10^6$ $cm^{-1}$ $M^{-1}$ in water; and a number average molecular weight ($M_n$) of about 5,000 to about 70,000.

In another aspect, a compound is provided including a dibenzosilole group substituted with one or more water-solubilizing groups. A representative compound provided herein has a structure represented by Formula (I):

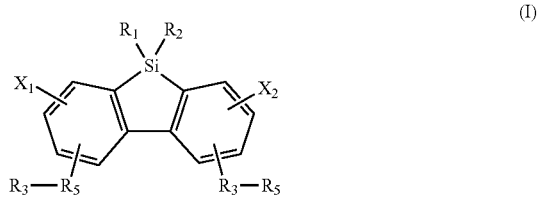

wherein, $R_1$ and $R_2$ independently are selected from the group consisting of H and optionally substituted $C_1$-$C_{20}$ alkyl, $C_{1-20}$ alkoxy, aryl and heteroaryl groups, fluorine, fluorine-containing groups (e.g., fluoroalkyl, fluoroaryl and fluoroheteroaryl), -L-W, wherein W is a water-solubilizing group and L is an optional linker, -L-Sc—, and -L-$R_x$—, wherein Sc is a conjugated substance and $R_x$ is a first reactive group;

$R_3$, $R_4$, and $R_5$ independently are selected from the group consisting of H and optionally substituted $C_1$-$C_{20}$ alkyl, $C_{1-20}$ alkoxy, and aryl or heteroaryl groups, fluorine, fluorine-containing groups (e.g., fluoroalkyl, fluoroaryl and fluoroheteroaryl), bromine, iodine, boron-containing groups (e.g., B(OR)$_2$, and BF$_3$), cyano, nitro, carboxyl, amides, ketones, phosphinoyl, phosphonates, sulfones and esters, -L-W, -L-$R_x$, and -L-Sc; and $X_1$ and $X_2$ independently are selected from the group consisting of H and optionally substituted $C_1$-$C_{20}$ alkyl, $C_{1-20}$ alkoxy, and aryl or heteroaryl groups, -L-W, -L-$R_y$, and -L-Sc, wherein $R_y$ is a second reactive group that is the same or different from $R_x$, wherein each L is independently selected from the group consisting of a single covalent bond, or L is a covalent linkage that is linear or branched, cyclic or heterocyclic, saturated or unsaturated, having 1-16 non-hydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds, provided that at least one of $R_1$-$R_5$, $X_1$ or $X_2$ is or comprises a water-solublilizing group (W).

In the structure of Formula (I), $R_x$ and $R_y$ independently can be an activated ester of a carboxylic acid, a carboxylic ester, an acrylamide, an acyl an azide, an alkyne, and alkene (e.g., allyl), an acyl nitrile, an aldehyde, an alkyl halide, an anhydride, an aniline, an amine, an aryl halide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol, and a photoactivatable group. In certain embodiments, $R_y$ can be independently selected from halide (e.g., Br or I), boronic acid, boronic acid ester (e.g., $C_1$-$C_6$ boronic acid ester), $C_1$-$C_6$ borane and BF$_3$ groups. In certain embodiments, $R_x$ is a carboxylic acid, or a succinimidyl ester of a carboxylic acid, a perfluorophenyl ester of a carboxylic acid, a sulfodichlorophenol (SDP) ester, a hydrazide, or a maleimide.

Representative examples of Sc include an amino acid, peptide, protein (e.g., antibody or fragment thereof, a phosphotidylserine-binding protein, a structural protein, a lectin, a tyramide, and an IgG binding protein, a fluorescent protein, a metal binding protein), nucleoside, nucleotide, nucleic acid base, oligonucleotide, or a nucleic acid polymer. In some embodiments, Sc is an enzyme, an enzyme inhibitor, an enzyme substrate, avidin or a derivative thereof (e.g., streptavidin or neutravidin) or a hapten (e.g., fluorescein, biotin, digoxigenin or DNP (2,4-dinitrophenyl)), a polysaccharide, psoralen, a drug, a hormone, a lipid, a lipid assembly, a synthetic polymer, a microparticle, a biological cell (e.g., animal or plant cell, bacterium, yeast or virus), a virus, a hapten, a biotin, a dextran, a hormone, a growth factor, a lectin, a lipopolysaccharide, a microorganism, a metal chelating moiety, or a peptide toxin.

Representative examples of W include alkylene oxide (e.g., ethylene glycol oligomers or polymers), sulfonate, thiosulfate, phosphonate, boronate, ammonium, carboxylate, alkylammonium and salts thereof.

Representative examples of L include a covalent linkage that is linear or branched, cyclic or heterocyclic, saturated or unsaturated, having 1-16 non-hydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; and aromatic or heteroaromatic bonds. In some embodiments, L is a covalent linkage (e.g., single, double or triple bond) and optionally substituted $C_1$-$C_6$ alkyl, $C_1$-$C_6$ alkoxy, ether, thioether, or alkyl thioether.

In certain embodiments, each of $R_1$ and $R_2$ is -L-W, wherein $R_1$ and $R_2$ are the same or different. For example, $R_1$ and $R_2$ can be independently selected from —(CH$_2$)$_y$—(OCH$_2$)$_x$—O—CH$_3$ and —(CH$_2$)$_y$—S—(CH$_2$O)$_x$—CH$_3$, wherein x is 1 to 20 and y is 1 to 6. In certain embodiments, $R_1$ and $R_2$ each is or comprises an allyl group. In certain embodiments, $R_3$, $R_4$ and $R_5$ is H. In certain embodiments, one or both of $X_1$ and $X_2$ is -L-$R_y$, wherein $X_1$ and $X_2$ are the same or different. In some embodiments, one or both of $X_1$ and $X_2$ is -L-Sc, wherein $X_1$ and $X_2$ are the same or different.

In another aspect, a compound is provided that has a structure represented by Formula (II), wherein $R_1$-$R_5$, $X_1$ and $X_2$ are as described above:

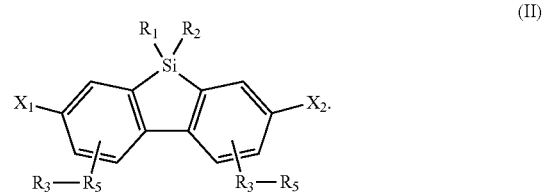

(II)

In yet another aspect, a compound is provided having a structure represented by Formula (III), wherein W is a water-solubilizing group, L is a linker, q is 1-3, and $X_1$, $X_2$, $R_3$, $R_4$, and $R_5$ are as described above:

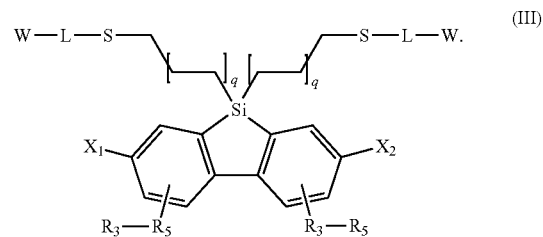

(III)

In yet another aspect, a polymer is provided that includes a monomer residue of a compound having a structure represented by Formula (III).

In yet another aspect, the polymer can include a monomer residue having a structure represented by Formula (IV) or Formula (V):

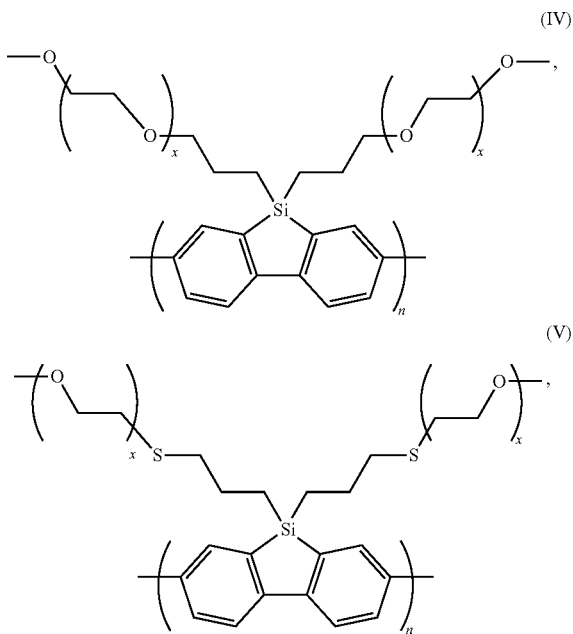

wherein n is 2 to 50; and x is 1 to 20. Polymers including monomer residues with a chemical structure represented by Formula (IV) or (V) homopolymer or can include one or more monomer residues of an optionally substituted arene or heteroarene.

Any of the polymers or compounds disclosed herein can be water-soluble. Thus, in another aspect, compositions are provided, including: a) a compound, polymer or conjugate as described herein; and b) an aqueous medium, wherein the compound, polymer or conjugate is dispersed in the aqueous medium.

In yet another aspect, a conjugate is provided, wherein a polymer or compound disclosed herein is linked to an affinity molecule (e.g., protein, nucleic acid, biotin, streptavidin). The conjugate can further include a target molecule, wherein the affinity molecule is associated with the target molecule (e.g., protein, nucleic acid, biotin, streptavidin). Also provided herein are kits for labeling cells that include: a) a conjugate as described herein, wherein the affinity molecule is capable of binding to a target molecule that is in or on the surface of a cell; and b) instructions for labeling the cell with the conjugate and detecting the labeled cell.

In yet another aspect, a method of labeling cells is provided, including contacting a cell with the polymer or conjugate as described herein for a time sufficient to allow the polymer or conjugate to bind to the surface of the cell or enter into the cell. The cell can be contacted with a conjugate as disclosed herein, wherein the affinity molecule binds to a target molecule on the surface of the cell.

In yet another aspect, a method for detecting a target molecule in a sample is provided. An exemplary method includes:
a) providing a sample that is suspected of containing a target molecule;
b) contacting the sample with a dibenzosilole polymer, as disclosed herein, wherein the polymer is conjugated to an affinity molecule that is capable of interacting with the target molecule in the sample, under conditions whereby the affinity molecule can bind to the target molecule, if present;
c) exciting the sample with light having an appropriate wavelength; and
d) detecting the light emitted from the polymer.

Also disclosed herein is a cell that includes a compound, polymer or conjugate as disclosed herein. The polymer, compound or conjugate can reside within the cytoplasm or nucleus of the cell, on or within a portion of the cell membrane, or is associated with the surface of the cell.

In yet another aspect, a composition is provided, including: a) a compound, polymer or conjugate as described herein; and b) an aqueous medium, wherein the compound, polymer or conjugate is dispersed in the aqueous medium.

In yet another aspect, a method of preparing a polymer is provided that includes
a) combining a plurality of reactive monomers to form a reaction mixture, wherein a first portion of the reactive monomers bear first reactive groups and a second portion of the monomers bear second reactive groups, wherein the first and second reactive groups are different and capable of reacting with each other to form a polymer, and wherein at least one reactive monomer comprises a dibenzosilole group substituted with one or more first water-solubilizing groups; and
b) subjecting the reaction mixture to conditions wherein the first and second reactive groups on the monomers react form a polymer.

In the method described herein, each reactive monomer can include a dibenzosilole group substituted with one or more first water-solubilizing groups monomers, thereby forming a homopolymer having a polymer backbone comprising residues of dibenzosilole monomers. The method can further include combining a third portion of reactive monomers, each bearing first reactive groups, second reactive groups, or a combination thereof, with the first and second monomer portions, wherein the third monomer portion comprises an optionally substituted arene or heteroarene group, thereby forming a copolymer having a polymer backbone comprising residues of arene or heteroarene monomers and dibenzosilole monomers. Each arene or heteroarene monomer can bear a second water-solubilizing group, wherein the first and second water-solubilizing groups are the same or different. In certain embodiments, the method includes polymerizing a plurality of first monomers having a structure represented by Formula (II), wherein $X_1$ and $X_2$ represent reactive groups suitable for participating in a polymerization reaction. The methods of making a polymer can include polymerizing the plurality of reactive monomers by Suzuki polymerization. In yet another aspect, a composition is provided, including: a) a compound, polymer or conjugate as described herein; and b) an aqueous medium, wherein the compound, polymer or conjugate is dispersed in the aqueous medium. In yet another aspect, a composition is provided, including: a) a compound, polymer or conjugate as described herein; and b) an aqueous medium, wherein the compound, polymer or conjugate is dispersed in the aqueous medium.

In yet another aspect, a method of producing a water-soluble, dibenzosilole derivative is disclosed that includes:
a) combining a compound having a structure represented by Formula (VI) and a second compound having a structure W-L-SH, wherein W is a water-solubilizing group, L is a linker, and SH is a thiol group, in a suitable solvent to form a reaction mixture; and
b) irradiating the reaction mixture with light to facilitate reaction between the first compound and the second compound, thereby producing a water-soluble compound having a structure represented by Formula (VII):

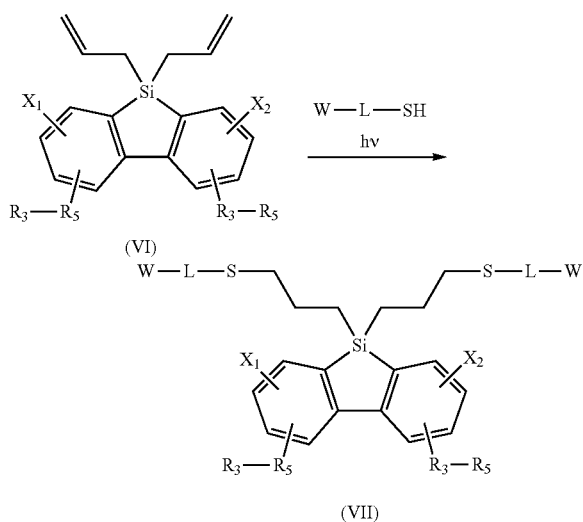

(VI)

(VII)

In certain embodiments, the method can include combining a first compound having a structure represented by Formula (VIII) or (IX) with the second compound:

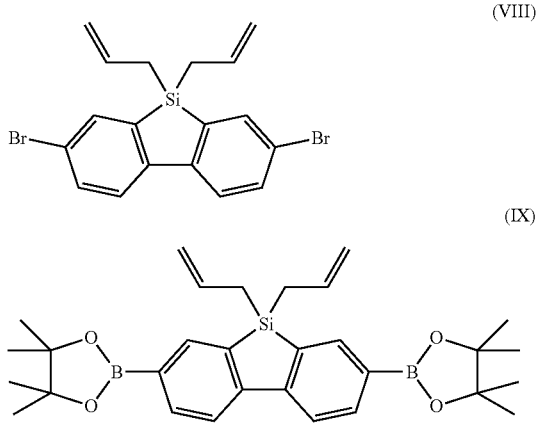

(VIII)

(IX)

In the methods disclosed herein W can be an ethylene glycol oligomer or polymer.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

FIG. 10 is a table that lists absorption wavelength maxima ($\lambda_{ab}$), emission wavelength maxima ($\lambda_{em}$), quantum yield (QY) and extinction coefficient for Pacific Blue™, Alexa Fluor® 405 and Compounds 13-29.

DETAILED DESCRIPTION OF THE INVENTION

Figure 1:
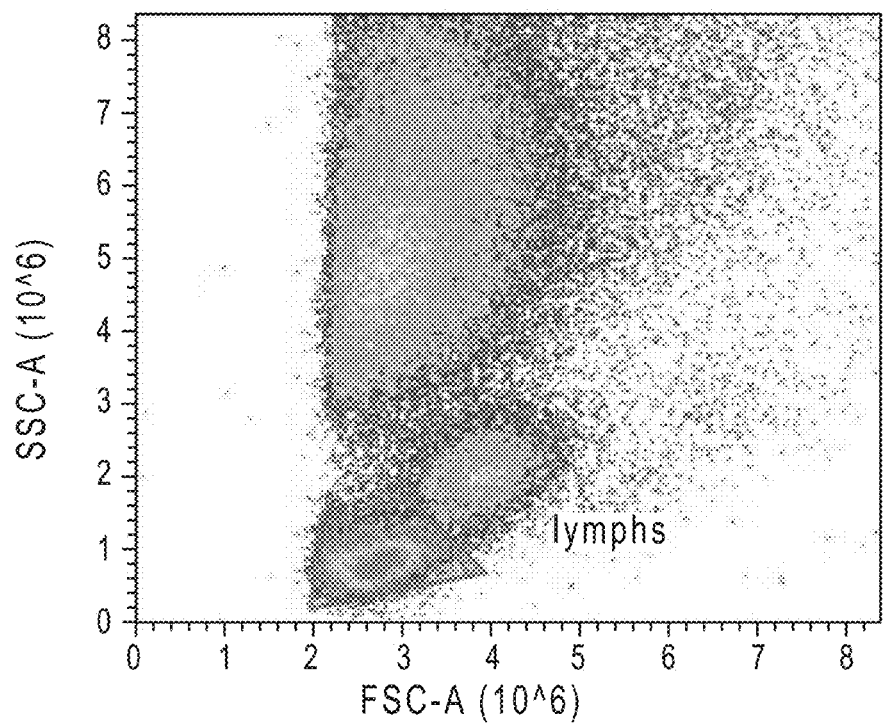
FIG. 1 is a multiparameter flow cytometry analysis for the sample described in Example 31.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "about", when used to describe a numerical value, shall encompass a range up to ±15% of that numerical value, unless the context clearly dictates otherwise.

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

A "conjugated polymer" as used herein refers to a polymer that contains an extended series of unsaturated bonds. The backbone of the conjugated polymer can contain alternating double and single bonds. A conjugated polymer can be conjugated along the full length of its backbone or can contain conjugated segments together with non-conjugated segments.

"Conjugated" is used herein to refer to an unsaturated organic system having adjacent atoms with pi electrons where there is overlap of a p-orbital with another across an intervening sigma bond. In larger atoms d-ortbitals can be involved. The atoms can be $sp^2$ or sp hybridized carbon atoms or other atoms with unshared electron pairs which can be hybridized into p orbitals.

"Water-soluble" is used herein refers to a material that is soluble in an aqueous-based solution, such as in water, water-based solutions or buffer solutions, including those used in biological or molecular detection systems. A "water-soluble" solution refers to a homogeneous solution containing fully dissolved material. A "water-soluble" dibenzosilole polymer is soluble in an aqueous-based solution at a concentration of >0.10 mg/mL. Incorporation of at least one "water-solubilizing group" into the material can increase the hydrophilicity of the material and can improve the solubility or dispersibility of the material in an aqueous environment.

"Arene" is used herein to refer to an aromatic hydrocarbon molecule with a conjugated cyclic molecular structure. Arenes can include monocyclic or polycyclic aromatic structures and can be optionally substituted at one or more substitutable positions. Representative examples of arenes include benzene, anthracene, naphthalene, indene and fluorene.

"Aryl" is used herein to refer to any organic radical derived from an arene by loss of one hydrogen atom. An aryl group can be formed from an aromatic ring or a plurality of fused aromatic rings and can be optionally substituted at one or more substitutable positions. Typical aryl groups contain 1 to 5 aromatic rings, which may be fused and/or linked Representative examples of aryl groups include phenyl, naphthyl, indenyl and fluoreneyl.

"Heteroarene" is used herein to refer to an arene in which at least one carbon atom in at least one aromatic ring is replaced by a heteroatom (e.g., nitrogen, oxygen, sulfur, and phosphorus), such that the aromaticity of the compound is retained, and can be optionally substituted at one or more substitutable positions. Examples of heteroarenes include thiophene, carbazole, pyridine, pyrimidine, furan, oxadiazole spirofluorene, indenofluorene, thienopyrazine, dithienosilole, quinoxaline, benzothiadiazole, thienobenzothiophene, thienothiophene and triarylamine.

"Heteroaryl" is used herein to refer to any organic radical derived from a heteroarene by loss of one hydrogen atom and can be optionally substituted at one or more substitutable positions. Exemplary heteroaryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl, perylene, perylene diimide, kidetopyrrolopyrrole, benzothiodiazol, benzoxadiazol, thienopyrazine and the like. Additional examples of heteroaryl groups include fused ring systems, such as, for example, benzofuryl, benzothienyl, benzopyrrolyl, dibenzofuryl, dibenzothienyl, phenanthrolinyl, carbazolyl and azacarbazolyl groups.

"Dibenzosilole" is used herein to refer to a compound having a fused aromatic ring structure similar to fluorene with the exception that the C9 carbon of fluorene is substituted with a silicon atom. A dibenzosilole optionally can be substituted at one or more substitutable positions as described herein. An organic radical derived from dibenzosilole by loss of one hydrogen atom is referred to herein interchangeably as a "dibenzosilole group" or "dibenzosilyl group." A compound that includes a dibenzosilole group that is substituted with one or more polymerizable groups is referred to herein as a "dibenzosilole monomer". Polymerizable groups can be attached to at any position of the dibenzosilole monomer; however, polymerizable groups typically are attached at the 2- and 7-positions of the dibenzosilole monomer. A polymer formed by polymerization of one or more dibenzosilole monomers is referred to herein as a "dibenzosilole polymer" or "poly(dibenzosilole)." A polymer that includes dibenzosilole groups that are linked through the 2 and 7 positions is also referred to as a "poly(2,7-dibenzosilole)." A dibenzosilole polymer can be a homopolymer that includes a plurality of linked dibenzosilole monomer residues. The monomer residues in a dibenzosilole homopolymer can include the same or different pendant groups. Alternatively, a dibenzosilole polymer can be a copolymer that includes one or more dibenzosilole monomer residues having the same or different pendant groups and one or more monomer residues that do not include a dibenzosilole group.

"Brightness" as used herein refers to product of a fluorophore's quantum yield (QY) and its extinction coefficient and is dictated by the following equation:

Brightness=(Quantum Yield)×(Extinction Coefficient)

"Quantum yield" or "QY" as used herein refers to the emission efficiency of a given fluorophore assessed by the number of times that a defined event, e.g., light emission, occurs per photon absorbed by the system. Unless otherwise noted, quantum yield is measured at room temperature. In other words, a higher quantum yield indicates greater efficiency and thus greater brightness of the described fluorophore or populations thereof.

"Extinction coefficient" as used herein refers to the molar extinction coefficient (also referred to as the "molar absorption coefficient" or "molar absorptivity") and is a measurement of how strongly a chemical species absorbs light at a given wavelength on a molar basis. The extinction coefficient (ε) is proportional to the absorbance of a sample according to the Beer-Lambert law, A=εcl, where absorbance, A, of a sample is dependent on the pathlength l and the concentration c of the species. Extinction coefficients can be calculated by measuring the absorbance of a sample of known concentration (within the limits of linearity) and using Beer's law to calculate extinction coefficient.

Provided herein are novel compounds and polymer compositions that include a dibenzosilole group and methods for preparing and using these compounds and polymer compositions. The compositions provided herein include one or more water-solubilizing groups. In certain embodiments, polymerizable monomers are provided that include a dibenzosilole group substituted with one or more water-solubilizing groups. Water-soluble, conjugated polymers including one or more water-solubilizing groups can render the polymer soluble in aqueous medium (e.g., water or buffers). Water-soluble polymers can be implemented in applications that require solubility in aqueous environments, such as are frequently used in life sciences applications.

Dibenzosilole compounds provided herein include at least one residue of a dibenzosilole monomer having a structure as represented in Formula (I):

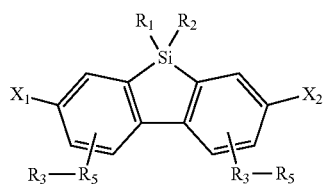

(I)

In Formula (I), $R_1$-$R_5$ are independently selected from H or $C_1$-$C_{20}$ alkyl, $C_{1-20}$ alkoxy, aryl and heteroaryl groups, fluorine, fluorine-containing groups (e.g., fluoroalkyl, fluoroaryl and fluoroheteroaryl), and can be optionally substituted at one or more positions. In some embodiments, $R_1$ and/or $R_2$ is an optionally substituted alkyl, alkyenyl or alkynyl group. For example one or both of $R_1$ and $R_2$ can be a $C_{4-10}$ alkyl, such as n-hexyl or n-octyl. Alternatively, one or more of $R_1$-$R_5$ can be -L-W, -L-Sc—, or -L-$R_x$—, wherein W is a water-solubilizing group, L is an optional linker, $S_c$ is a conjugated substance and $R_x$ is a reactive group.

$X_1$ and $X_2$, which can be the same or different, independently are selected from the group consisting of H and optionally substituted $C_1$-$C_{20}$ alkyl, $C_{1-20}$ alkoxy, and aryl or heteroaryl groups, -L-W, -L-$R_y$, and -L-Sc, wherein $R_y$ is a second reactive group that is the same or different from $R_x$.

The reactive group can be used to couple the dibenzosilole monomer to another material (e.g., a protein, hapten, nucleic acid, or a solid support) to form a conjugate. Certain compounds provided herein include a reactive group that is suitable for coupling to a substance using a cycloaddition reaction (e.g., click chemistry). For example, the compound can be substituted either directly or through a linker to a terminal or cyclic alkyne (e.g., dibenzocyclooctyne, DIBO) or an azide group. Alternatively, the reactive group (also referred to herein as a "polymerizable group") can facilitate incorporation of the dibenzosilole monomer into a growing polymer chain during a polymerization reaction. Representative examples of reactive groups include a carboxylic acid, an activated ester (e.g., succinimidyl ester) of a carboxylic acid, a carboxylic ester, an acrylamide, an acyl an azide, an alkynyl, an acyl nitrile, an aldehyde, an alkyl halide, an anhydride, an aniline, an amine, an aryl halide, an aziridine, a boronate, a diazoalkane, a haloacetamide, a halotriazine, a hydrazide, a hydrazine, an imido ester, an isocyanate, an isothiocyanate, a maleimide, a phosphoramidite, a reactive platinum complex, a silyl halide, a sulfonyl halide, a thiol, and a photoactivatable group.

In some embodiments, the reactive group can be directly or indirectly through a linker attached to the silicon atom within the silole ring. For example, $R_1$ and/or $R_2$ can include a reactive group. Representative examples of reactive groups that can be attached to the silicon atom include allyl, haloalkyl, carboxyalkyl, hydroxyalkyl, alkoxycarbonylalkyl, thioalkyl and alkenyl groups. Certain dibenzosilole compounds provided herein include reactive groups that can be polymerized (also referred to herein as "polymerizable groups") to form a dibenzosilole polymer. In certain embodiments, the compound includes functional groups appropriate for a Suzuki polymerization reaction, such as a halide or boron-containing functional group. Suitable halides include bromine or iodine, although other halide-containing groups, such as chlorine, triflate ($CF_3SO_3^-$) tosylate and mesylate also can be used. Representative examples of boron-containing functional groups include $BF_3$ group, boronic acid (—$B(OH)_2$), boronic esters (—$B(OR^1)$ $(OR^2)$ or —$B(OR^5O)$) and borane groups (i.e., —$BR^3R^4$), wherein $R^1$ is a substituted or non-substituted $C_1$-$C_6$ alkyl group and $R^2$ is H or a substituted or non-substituted $C_1$-$C_6$ alkyl group; $R^3$ and $R^4$ are each independently substituted or non-substituted $C_1$-$C_6$ alkyl groups, and $R^5$ is a substituted or non-substituted divalent hydrocarbon radical resulting in a 5 or 6 membered ester ring. Examples of suitable groups as $R^5$ include substituted or non-substituted $C_2$ or $C_3$ alkylene groups, or substituted or non-substituted ortho- or meta-phenylene groups. Suitable boronic ester groups include, for example, products of esterification of the corresponding boronic acid group with monovalent $C_1$-$C_6$ alcohols, ethane diols such as pinacol, propane diols or ortho aromatic diols such as 1,2-dihydroxybenzene.

In certain embodiments, the dibenzosilole monomer is substituted with two polymerizable groups, which can be the same or different. Suitable polymerizable groups for such disubstituted monomers include a halide (e.g., Br or I), boronic acid, boronic acid ester (e.g., $C_1$-$C_6$ boronic acid ester), $C_1$-$C_6$ borane or $BF_3$ group.

Typically, dibenzosilole monomer units are linked through the 2- and 7-positions of the group to maximize conjugation through the repeat unit, as shown in the structure represented by Formula (II):

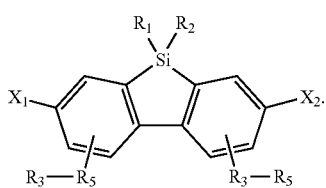

(II)

However, polymerizable groups can reside at any position within the benzene ring of the dibenzosilole monomer and polymers with non-2,7 linkages can have certain advantages depending on the application. For example, non-2,7-linked dibenzosilole polymers can have a wider bandgap and a higher triplet energy level than the corresponding 2,7-linked versions.

Dibenzosilole compounds described herein can be substituted with one or more water-solubilizing groups (W), which can be the same or different. In certain dibenzosilole compounds, at least one of $R_1$-$R_5$, $X_1$ or $X_2$ is or comprises a water-solublilizing group (W). In other compounds, only $R_1$ and/or $R_2$ include the water-solubilizing group. Water-solubilizing groups increase the hydrophilicity of the compound. Certain dibenzosilole derivatives bearing water-solubilizing substituents described herein are sufficiently hydrophilic, such that they can be dispersed or dissolved in aqueous medium. The water-solubilizing group can carry a positive or negative charge. In some embodiments, the water-solubilizing group does not carry a positive or negative charge. Incorporation of uncharged water-solubilizing groups (e.g., polyethylene glycols) can provide a dibenzosilole polymer having no net charge. For example, uncharged polymers may provide lower levels of non-specific binding to certain hydrophobic or cellular surfaces. Representative examples of water-solubilizing groups include carboxylic acids, amines, sulfonic acids, sulfonates, thiosulfate, phosphonate, boronate, ammonium, alkylammonium, alcohols, ethers, polyethers, amides, sulphonamides and derivatives and salts thereof and the like. Additional examples of water-solubilizing groups include non-charged, hydrophilic groups such as saccharides and polysaccharides (e.g., dextrans).

Water-solubilizing groups also include those having one or more alkylene oxide repeat units. For example, the water-solubilizing group can contain one or more ethylene glycol units, —(OCH$_2$CH$_2$)—. Ethylene glycol oligomers or polymers are referred to herein as a "polyethylene glycol" (PEG) group. The PEG group can be any length, however, typically includes between 1 to 20 ethylene glycol repeat units. In certain embodiments, PEG groups having more than 20 ethylene glycol repeat units are used. An exemplary PEG group is —(OCH$_2$)$_x$—O—CH$_3$, wherein x is 1 to 20.

The water-solubilizing group, reactive group or conjugated substance can be attached to the dibenzosilole group through a linker (L). L can be covalent linkage (e.g., single, double or triple bond). The covalent linkage can be linear or branched, cyclic or heterocyclic, saturated or unsaturated, having 1-16 non-hydrogen atoms (e.g., C, N, P, O or S), such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds. Representative examples of linkers include, e.g., optionally substituted $C_1$-$C_6$ alkyl, $C_1$-$C_6$ alkoxy, ether, thioether, and alkyl thioether groups.

In certain embodiments, the silicon atom of the silole group can be linked to one or two water-solubilizing groups (e.g., PEG), typically via a linker, such as an alkylene linker having about 1 or more alkylene repeat units. For example, the linker can include a chain of one or more (e.g., 1-6) methylene groups. In certain embodiments, the alkylene linker further includes a thioether group (e.g., a (CH$_2$)$_y$—S—) that is attached to the water-solubilizing group. For example, in certain compounds, $R_1$ and/or $R_2$ groups can include one of the following structures: —(CH$_2$)$_y$, —(OCH$_2$)$_x$—O—CH$_3$ or —(CH$_2$)$_y$—S—(CH$_2$O)$_x$—CH$_3$, wherein x is 1 to 20 and y is 1 to 6.

Thus, in certain embodiments, dibenzosilole compounds are provided having a structure as shown in Formula (III):

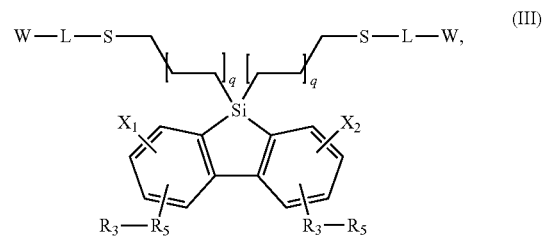

(III)

wherein q is 1-3, and W, L, $X_1$, $X_2$, $R_3$, $R_4$, and $R_5$ are as defined herein. Although not required, $X_1$ and $X_2$ typically are linked to the 2- and 7-positions of the group.

Dibenzosilole compounds can be linked to a substance to form a conjugate. Conjugated substances ($S_c$) include, for example, amino acids, peptides and proteins (e.g., antibodies or fragments thereof, fluorescent protein, and metal binding protein); nucleosides, nucleotides, nucleic acid bases, oligonucleotides, and nucleic acid polymers (e.g., DNA or RNA); and microorganisms, such as a biological cell (e.g., animal or plant cell, bacterium, yeast) or virus. Further examples of conjugated substances include avidin or a derivative thereof (e.g., streptavidin, neutravidin); and haptens (e.g., fluorescein, biotin, digoxigenin or DNP (2,4-dinitrophenyl)). In certain embodiments, the conjugate includes a dibenzosilole compound linked to an antibody, an antigen, streptavidin or biotin. Other conjugated substances include enzymes and polysaccharides (e.g., dextrans). Dibenzosilole compounds provided herein also can be associated (e.g., covalently or non-covalently bonded) to a dye, semiconductor nanocrystal, or synthetic polymer. Alternatively, or in addition, dibenzosilole compounds can be attached to a solid support, e.g., particles (e.g., nanoparticles, microparticles, magnetic or non-magnetic beads), films, well plates, containers, and the like.

Also provided herein is a water-soluble polymer that includes a backbone formed from a plurality of linked monomer residues, and at least one monomer residue within the polymer backbone comprises a dibenzosilole group. The dibenzosilole polymers provided herein further include at least one water-solubilizing group that facilitates solubilization of the polymer in an aqueous medium (e.g., an ethylene glycol oligomer or polymer, sulfonate, thiosulfate, phosphonate, boronate, ammonium, carboxylate or salt thereof). Thus, provided herein is a polymer that includes and at least one monomer residue that is substituted with one or more water-solubilizing groups. The water-solubilizing group can be a substituent on the dibenzosilole group or on another monomer residue within the polymer backbone. For example, the polymer can include a dibenzosilole residue that can bears a water-solubilizing group and an aromatic residue (e.g., arene or heteroarene) that bears the one or more water-solubilizing pendant group that can be the same or difference than the water-solubilizing group on the dibenzosilole residue.

The polymer can be a homopolymer or a copolymer or oligomer including one or more dibenzosilole monomer residues and can be a linear or a branched polymer. Dibenzosilole copolymers can be alternating, random and block polymers where the percentage of each monomer used to prepare the polymer may vary. The polymer can include monomer residues that provide additional conjugation such that their presence does not disrupt the conduction of electrons through the polymer or significantly degrade the optical properties of the polymer. Incorporation of additional aromatic monomer repeat units into dibenzosilole polymers provided herein can be used to tailor both the energy levels of the polymer and the stability of the resulting compositions. In addition, incorporation of such groups into the polymer can be used to optimize light absorption, ionization potential, and/or electronic properties of the polymer for particular applications. For example, copolymerization of dibenzosilole monomers with other types of conjugated monomers (e.g., arenes or heteroarenes) can provide conjugated polymers with altered fluorescence excitation and emission profiles.

Thus, also provided herein are conjugated polymers having a backbone formed from one or more monomer residues that include an aromatic group that is different from the dibenzosilole group. The aromatic group, which can be substituted or unsubstituted, can be an arene or heteroarene. Representative examples of aromatic groups for copolymerization with dibenzosilole monomer residues described herein include, benzene, naphthalene, fluorene, thiophene, carbazole, pyridine, pyrimidine, spirofluorene, indenofluorene, thienopyrazine, dithienosilole, quinoxaline, benzothiadiazole, thienobenzothiophene, thienothiophene and triarylamine groups. Copolymers including a plurality of linked dibenzosilole and aromatic monomer residues can be further linked to substances to form conjugates, as described herein.

Also provided are conjugated, fluorescent copolymers that include one or more dibenzosilole monomer residues, as described herein, and one or more optionally substituted arene or heteroarene monomer residues. Dibenzosilole copolymers and conjugates of such copolymers can further include at least one water-solubilizing group linked to one or more dibenzosilole and/or aromatic residues of the polymer to improve the hydrophilicity of such copolymers. Thus, also provided are hydrophilic and water-soluble copolymers that include a conjugated backbone formed from linked dibenzosilole and arene and/or heteroarene monomer residues, wherein one or more of the dibenzosilole and/or arene or heteroarene monomer residues bear a water-solubilizing group. In certain embodiments, conjugated copolymers are provided that include a backbone formed from residues of one or more dibenzosilole monomers, as described herein, and one or more optionally substituted fluorene monomers, wherein one or more of the dibenzosilole and/or fluorene monomer residues bears a water-solubilizing group.

Dibenzosilole polymers can range in size, depending on the polymerization conditions, catalysts, and types and amounts of monomers utilized in the polymerization reaction. For example, the polymer can have a number average molecular weight ($M_n$) of about 5,000 to about 100,000. Polymers with $M_n$ of about 30,000 to about 70,000 can be water-soluble and are not prone to aggregation in aqueous medium. Typically dibenzosilole polymers provided herein have a narrow range of molecular weights. For example, the polydispersity of the polymers provided herein can be expressed in terms of a polydispersity index (PDI). Polymers provided herein can have a PDI ranging from about 1.2 to 2.2, where a polymer with a PDI from about 1.0 to about 1.5 can be considered monodisperse. In certain embodiments, the polymers have a $M_w$ of about 42,000-70,000 Daltons, with narrow distribution of PDI≤1.5.

Dibenzosilole polymers are provided herein that are soluble in common organic solvents (e.g., THF, dichloromethane, methanol, toluene, and the like). Certain polymers described herein also are soluble in aqueous media, such as, for example, water, saline, buffered aqueous solutions (e.g., borate, carbonate, or phosphate buffer) and the like. Aqueous compositions can include a dibenzosilole polymer or conjugate thereof, as described herein, that is dissolved or dispersed in an aqueous medium. Typically, polymers provided herein exhibit aqueous solubility up to 1.0 mg/mL in water or buffers such as PBS.

Dibenzosilole polymers disclosed herein include a conjugated segment. Extended conjugation within the polymer backbone allows the polymer to exhibit fluorescence emission upon excitation at an appropriate wavelength of light. Fluorescent dibenzosilole polymers that include a conjugated segment can have a tunable photophysical property in the near ultraviolet (UV) to far infrared (IR) range. Because the disclosed polymers exhibit a host of favorable optical properties, this class of polymers is ideal for use in biological assays requiring a high level of sensitivity. For example, polymers provided herein emit bright, visible light upon UV excitation and typically absorb light having a wavelength of about 500 nm or less (e.g., about 300 nm to about 500 nm). In certain embodiments, the disclosed polymers absorb light having a wavelength of about 350 nm to about 450 nm; or about 380 nm to about 410 nm. Polymers that can absorb light having a wavelength of about 405 nm can be effectively irradiated using a violet laser. Upon irradiation at an appropriate wavelength, dibenzosilole polymers can emit light having a wavelength of greater than about 400 nm; e.g., about 400 to about 800 nm; or about 400-780 nm. Incorporation of additional aromatic monomer residues (e.g., benzodithiazole, phenyl or thiophenyl) in the polymer backbone can alter the electronic properties of the polymer and shift the excitation and emission wavelength of the copolymer.

The disclosed polymers are photostable and do not dim significantly when dissolved in an aqueous medium. By virtue of their high extinction coefficients and high quantum yield, dibenzosilole polymers described herein are exceptionally bright, where brightness is a function of quantum yield and extinction coefficient. In addition, dibenzosilole polymers exhibit minimal shifts in emission peak that can result from high intensity and/or prolonged irradiation, making them particularly useful in applications that utilize high intensity lasers (e.g., cell imaging and flow cytometry). For example, fluorescent dibenzosilole polymers described herein typically exhibit an extinction coefficient of greater than about $0.5 \times 10^6$ $cm^{-1}M^{-1}$, when irradiated at 405 nm; and routinely exhibit quantum yields of greater than 20% (e.g., greater than 40%; or greater than 50%; or greater than 60%; or greater than 70%) in aqueous solution.

In certain embodiments, the polymers have a quantum yield of about 40% to about 70% and an extinction coefficient of 1,000,000 $cm^{-1}M^{-1}$ or greater, when measured at an excitation wavelength of 405 nm. In certain embodiments, the polymers have a quantum yield of about 40% or greater and an extinction coefficient of about 1,000,000 $cm^{-1}M^{-1}$ to about 2,500,000 $cm^{-1}M^{-1}$, when measured at an excitation wavelength of 405 nm. In certain embodiments, the polymers have a quantum yield of about 50% or greater and an extinction coefficient of about 1,000,000 $cm^{-1}M^{-1}$ to about 2,500,000 $cm^{-1}M^{-1}$, when measured at an excitation wavelength of 405 nm. In other embodiments, the polymers have a quantum yield of about 60% or greater and an extinction coefficient of about 1,000,000 $cm^{-1}M^{-1}$ to about 2,500,000 $cm^{-1}M^{-1}$, when measured at an excitation wavelength of 405 nm. In yet other embodiments, the polymers have a quantum yield of about 60% or greater and an extinction coefficient of about 2,000,000 $cm^{-1}M^{-1}$ to about 2,500,000 $cm^{-1}M^{-1}$ when measured at an excitation wavelength of 405 nm. In yet other embodiments, the polymers have a quantum yield of about 70% or greater and an extinction coefficient of about 2,000,000 $cm^{-1}M^{-1}$ to about 2,500,000 $cm^{-1}M^{-1}$ when measured at an excitation wavelength of 405 nm.

Also provided herein are novel methods of synthesizing dibenzosilole compounds that bear one or more water-solubilizing groups. The methods disclosed herein can provide dibenzosilole derivatives that can be used to form water-soluble conjugates with various substances (e.g., biological molecules). The synthetic methods also can provide water-soluble dibenzosilole monomers that can be polymerized to form a conjugated, water-soluble dibenzosilole homopolymer or copolymer.

In general, water-soluble dibenzosilole compounds can be prepared by coupling a reactive dibenzosilole compound to one or more reactive water-solubilizing groups. The reactive functional group can be attached directly or indirectly through a linker to either fused benzene ring or to the silicon atom of the silole ring. In certain embodiments, methods are provided for coupling a reactive water-solubilizing group to a reactive functional group that is attached directly or indirectly through a linker to either fused benzene ring. Coupling chemistries that can be used for linking reactive functional groups to a water-solubilizing group are well known in the art. Representative examples of reactive groups that can be used for coupling substitutable groups of the dibenzosilole compound to a water-solubilizing group include a carboxylic acid, an activated ester (e.g., succinimidyl ester) of a carboxylic acid, a carboxylic ester, an acrylamide, an acyl, an azide, an alkyne, an acyl nitrile, an aldehyde, an alkyl halide, an anhydride, an allyl, an aniline, an amine, an aryl halide, an aziridine, a boronate, a diazoalkane, a haloacetamide, a halotriazine, a hydrazide, a hydrazine, an imido ester, an isocyanate, an isothiocyanate, a maleimide, a phosphoramidite, a reactive platinum complex, a silyl halide, a sulfonyl halide, a thiol group and photoactivatable groups such as, for example, an aryl azide, a benzophenone or a diazirine.

In other embodiments, the reactive functional group can be attached directly or indirectly through a linker to the silicon atom of the silole ring. Thus, provided herein are novel methods for derivatization of the silicon atom of a dibenzosilole compound. In addition, methods are provided for attaching water-soluble groups (e.g., alkylene oxides) to the silicon atom of dibenzosilole. Typically, introduction of alkyl substituents at C9 of fluorene can be accomplished by treating the fluorene with a strong base (e.g., KOH, NaOH, $NaOCH_3$ or n-BuLi) followed by treatment with an electrophilic alkylating agent to provide the resulting C9-alkylated derivative. Using this general method, alkyl-bearing substituents can be readily attached to the pentene ring of fluorene. The replacement of carbon with silicon in the pentene ring of fluorene, however, dramatically alters the reactivity of the compound. While not wishing to be bound by theory, differences in reactivity are the result, at least in part, of silicon having lower electronegativity than carbon. Because the hydrogen atoms bound to silicon are less acidic than those attached to carbon, standard hydrocarbon alkylating chemistries are not effective for coupling alkyl-bearing groups directly to the silicon atom of dibenzosilole. In addition, treatment of dibenzosilole compounds with a strong base such as used in typical alkylation reactions is particularly harsh and can destroy the molecule. For example, standard transalkylation reactions of dibenzosilole groups typically involve treatment of 9,9-dimethyl-3,6-(trimethylsilyl)dibenzosilole with a slight excess of alkyl-lithium to form the corresponding 9,9-dialkyl-3,6-(trimethylsilyl)dibenzosilole (see, e.g., U.S. Pat. No. 6,353,072). Subsequent iododesilation of 9,9-dialkyl-3,6-(trimethylsilyl)dibenzosilole with iodine monochloride yields 9,9-dialkyl-3,6diiododibenzosilole. Surprisingly, transalkylation reactions did not prove effective for introducing ethylene glycol oligomers at the 9-position of dibenzosilole under the same reaction conditions. For example, when 2,5,8,11,14-pentaoxapentadecane and 2,5,8,11,14,17,20,23,26,29,32-undecaoxatetratriacontan-34-ol) were utilized, these compounds failed to survive selective desilation with iodine monochloride.

The methods provide an alternative to standard transalkylation methods that are not suitable for use with the dibenzosilole compounds provided herein. In general, the disclosed methods can be used for alkylating any type of silole compound. More specifically, methods are provided for attaching an alkyl-bearing compound to silicon to provide a 9-substituted dibenzosilole derivative. The disclosed methods involve attaching alkyl groups at the silicon atom of the dibenzosilole ring that provide an alternative to transalkylation reactions typically used to convert methyl groups at the 9-position of dibenzosilole into a longer alkyl group, but without decomposition of the substituents.

In one method, alkylation at silicon is achieved by coupling an alkylating agent bearing a reactive alkyl group to a reactive derivative of dibenzosilole. The coupling chemistries provided herein can utilize an alkylating agent that bears a reactive thiol group (e.g., mercaptan). In a representative method, a dibenzosilole derivative that is substituted with a photoactivatable pendant group on silicon is photochemically coupled to a mercaptan to provide a 9-alkylated dibenzosilole derivative. Examples of suitable photoactivable pendant groups include allyl and vinyl groups. Suitable mercaptans include any type of group that is terminated with a thiol group, such as, for example, 1-ethanethiol, 1-butanethiol, 4-mercaptohexanoiv acid and 4-mercapto-1-butanol. In certain methods, the mercaptan includes a water-solubilizing group and a thiol functional group. For example, the water-solubilizing group can be a thiol-substituted ethylene glycol oligomer or polymer, such as, for example, 0-(2-mercaptoethyl)-0'-methyl-hexa(ethylene glycol), 0-(2-mercaptoethyl)-0'-methylpolyethylene glycol oligomers, or $H_3CO-[CH_2CH_2O-]_nCH_2CH_2SH$ where n can be an integer between 2 and about 100.

A representative method involves photochemically coupling a mercaptan (i.e., UV-initiated thiol-ene coupling reaction) to a dibenzosilole derivative bearing two diallyl groups linked to the silole ring as shown in the structure represented by Formula (VI):

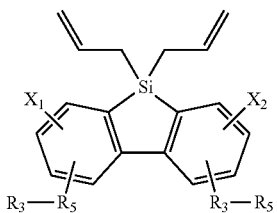

(VI)

In general, a compound having a structure represented by Formula (VI), where $X_1$, $X_2$ and $R_3$-$R_5$ are as defined above, is combined with an alkylating agent bearing a reactive thiol group in a suitable solvent to form a reaction mixture. Irradiation of the reaction mixture with light for an appropriate length of time initiates reaction between the thiol group and the allyl groups of the dibenzosilole compound.

Also provided herein are methods for coupling a reactive water-solubilizing group to the silicon atom within the silole ring. In one particular method, water-soluble dibenzosilole compounds are prepared by photochemically coupling a dibenzosilole derivative that is substituted with a photoactivatable pendant group (e.g., allyl) to a mercaptan bearing a water-solubilizing group (e.g., PEG thiol). A compound having a structure represented by Formula (VI) can be combined with a compound having a structure represented as W-L-SH, wherein W is a water-solubilizing group, L is an optional linker, and SH is a thiol group, in a suitable solvent to form a reaction mixture. Irradiation of the reaction mixture with light for an appropriate length of time produces a water-soluble dibenzosilole derivative having a structure represented by Formula (VII):

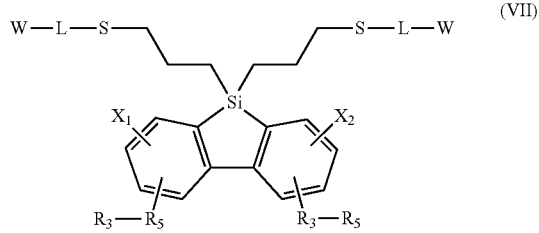

(VII)

In certain embodiments, a dibenzosilole derivative bearing two allyl substituents and polymerizable groups at the 2- and 7-positions of the dibenzosilole group, as shown in the structures represented by Formula (VIII) or (IX), where $X_1$, $X_2$, L, W and $R_3$-$R_5$ are as defined above, is combined with a thiol derivative of water-solubilizing group (e.g., PEG) in a suitable solvent to form a reaction mixture and then irradiated with light to provide a water-soluble dibenzosilole derivative bearing polymerizable groups at the 2- and 7-positions of the dibenzosilole group. Polymerization of monomers having the structure represented in Formula (VI) can provide a dibenzosilole polymer that includes a plurality of water-solubilizing pendant groups linked to the backbone of the polymer.

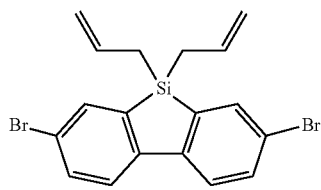

(VIII)

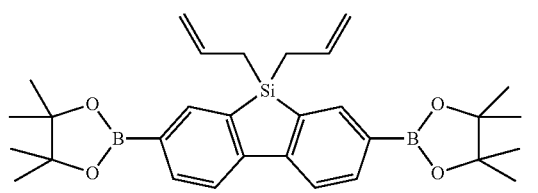

(IX)

Representative examples of monomers that can be prepared from compounds having structures represented by Formula (VIII) or Formula (IX) according to the methods described herein include those represented by the structures shown in FIG. 5A-FIG. 5D.

Figure 5A:
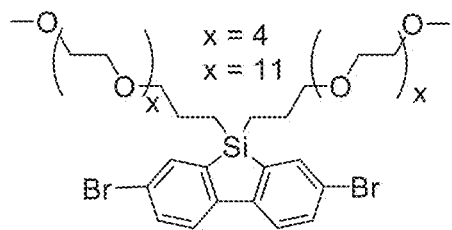
FIG. 5A is a representative monomer that can be prepared from compounds having structures represented by Formula (VIII).
Figure 5B:
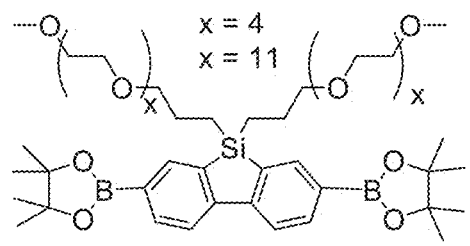
FIG. 5B is a representative monomer that can be prepared from compounds having structures represented by Formula (IX).
Figure 5C:
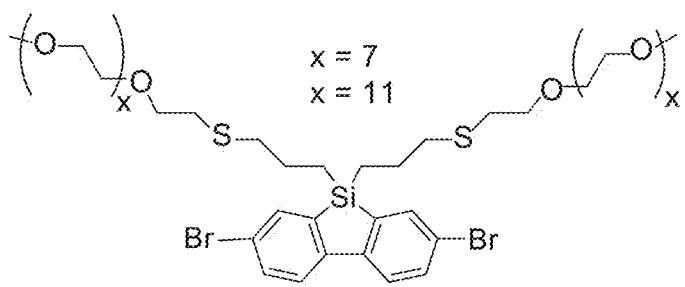
FIG. 5C is a representative monomer that can be prepared from compounds having structures represented by Formula (VIII).
Figure 5D:
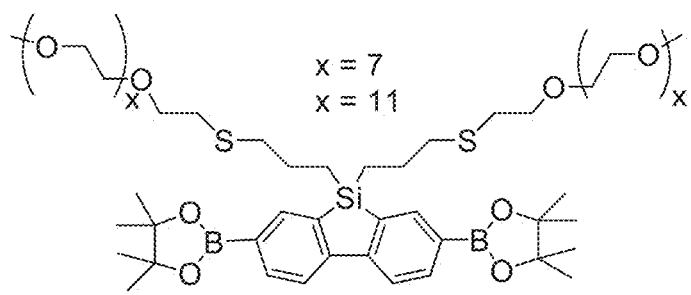
FIG. 5D is a representative monomer that can be prepared from compounds having structures represented by Formula (IX).
Figure 5E:
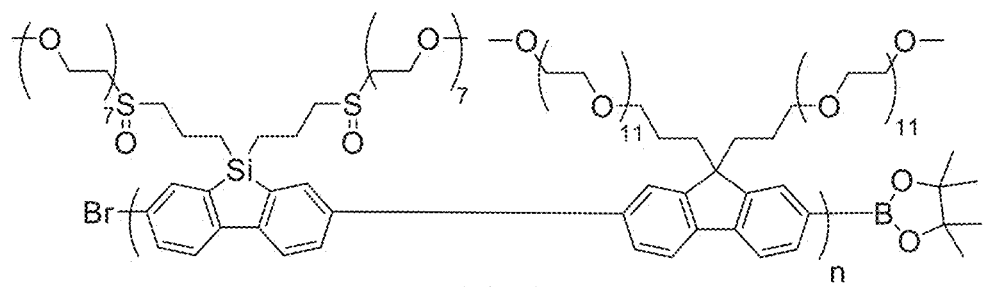
FIG. 5E is a representative compound prepared from monomers described herein in which the sulfur atoms of the pendant groups have been oxidized as sulfones.
Figure 5F:
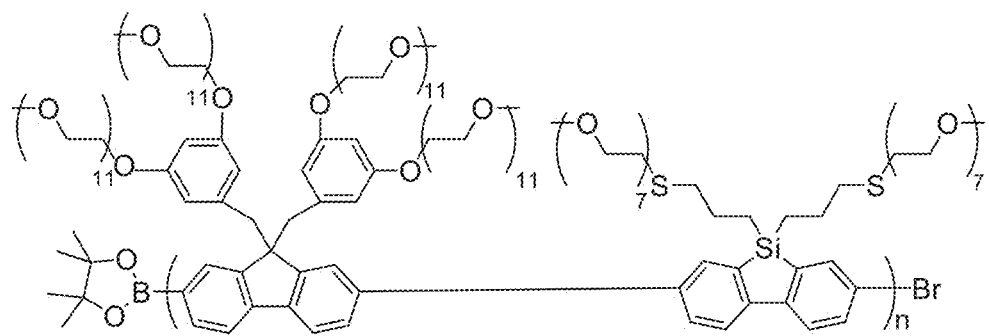
FIG. 5F is a representative dibenzosilole polymer that can be prepared by polymerization reactions provided herein.
Figure 5G:
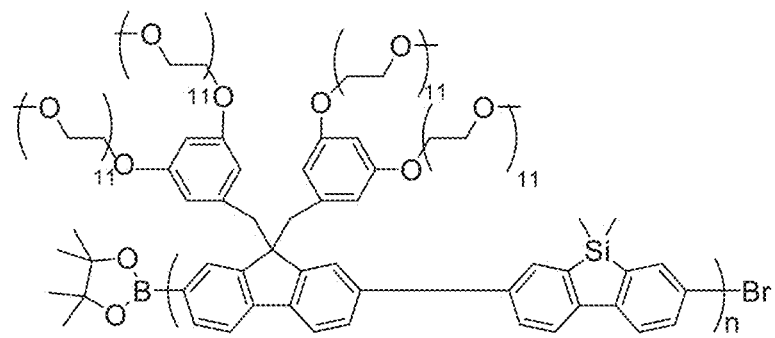
FIG. 5G is a representative dibenzosilole polymer that can be prepared by polymerization reactions provided herein.

Additional examples of compounds prepared from monomers described herein include those in which the sulfur atoms of the pendant groups have been oxidized as sulfoxides and sulfones, such as represented by the structure shown in FIG. 5E and those represented by the structures shown in FIG. 5F and FIG. 5G, where n represents the number of repeating units.

Also provided herein are novel methods for preparing conjugated polymers including one or more dibenzosilole repeat units. Thus, polymerization methods are provided for preparing a conjugated polymer that includes a backbone formed of linked aromatic residues, wherein at least one of the monomer residues includes a dibenzosilole group. Compounds provided herein can include polymerizable and water-solubilizing substituents that can be used to prepare water-soluble dibenzosilole polymers and copolymers. Also disclosed are methods for preparing water-soluble, conjugated copolymers that include one or more dibenzosilole monomer residues and one or more aromatic residues.

A general method for preparing a dibenzosilole polymer as described herein involves combining a plurality of reactive monomers to form a reaction mixture, wherein a first portion of the reactive monomers bears first reactive groups and a second portion of the monomers bears second reactive groups, wherein the first and second reactive groups are different and capable of reacting with each other to form a polymer. At least one reactive monomer includes a dibenzosilole group that is optionally substituted with one or more water-solubilizing groups. The reaction mixture then is subjected to conditions wherein the first and second reactive groups on the monomers react form a polymer. In some methods, a plurality of dibenzosilole monomers bearing suitable polymerizable groups are condensed to produce a poly(dibenzosilole) that includes a polymer backbone formed of the linked dibenzosilole monomer residues.

Various types of polymerization strategies can be employed to couple the polymerizable monomers described herein. One representative method for preparing conjugated polymers described herein involves Yamamoto polymerization of monomers bearing halide functional groups in the presence of a metal catalyst (e.g., nickel). Another polymerization strategy involves Suzuki polycondensation. The Suzuki reaction is a Pd-catalyzed coupling reaction between an aromatic boronic acid derivative and an aromatic halide that yields the corresponding biphenyl. In general, Suzuki polymerization involves the coupling aromatic monomers that are each provided with two reactive functional groups. Appropriate functional groups for Suzuki polymerization include halides (e.g., Br or I) and boron-containing functional groups, such as boronic acid, a boronic ester (e.g., C1-C6 boronic acid ester), a borane group (e.g., C1-C6 borane) and $BF_3$ groups. In one exemplary method, a first reactive dihalide monomer is polymerized with a second monomer having two boron derivative functional groups. In this arrangement the first and the second monomers can be the same to produce a homopolymer or different to produce a copolymer. In a second exemplary method, a monomer having a boron derivative functional group and a reactive halide functional group is polymerized to form a homopolymer. Copolymers can be prepared using such an arrangement by polymerizing together two or more different types of monomers each containing both functionalities.

A representative Suzuki polymerization reaction involves forming a reaction mixture that includes (a) an aromatic monomer having at least two reactive boron-containing groups and an aromatic monomer having at least two reactive halide functional groups; or (b) an aromatic monomer having one reactive halide functional group and one reactive boron-containing group. The reaction is conducted in a solvent in which the conjugated polymer is soluble. Suitable solvents include water-miscible, polar solvents such as THF, acetone and chloroform. Included in the reaction mixture is a catalytic amount of a catalyst to catalyze the polymerization of the aromatic monomers. The reaction can be catalyzed using a soluble Pd source. Pd (II) salts (e.g., Pd acetate) or Pd (0) complexes such as $Pd(Ph_3P)_4$ are examples of suitable Pd sources that can be used in the methods disclosed herein. The reaction also includes a base in an amount sufficient to convert the reactive boron-containing functional groups into anionic —$BX_3^-$— groups, wherein X is independently F or OH. Suitable bases include inorganic base, such as, for example, alkali metal carbonates or bicarbonates, such as potassium or sodium bicarbonate.

In certain methods, dibenzosilole monomers having a structure as represented in Formula (II) are polymerized via Suzuki polycondensation to produce a 2, 7-linked dibenzosilole polymer. For example, dibromo and bis(boronate) 2, 7-disubstituted dibenzosilole monomers can be polymerized as described herein to yield a poly(2,7-dibenzosilole). The polymerization reaction can utilize dibenzosilole monomers as described herein, which can optionally bear one or more water-solubilizing groups. Addition of aromatic monomers (e.g., arenes or heteroarenes) bearing suitable polymerizable groups into the reaction mixture can provide copolymers having a backbone that includes linked dibenzosilole and aromatic monomer residues. In certain methods, the additional monomers can include optionally substituted arene (e.g., fluorene) or heteroarene groups, thereby forming a copolymer having a polymer backbone comprising residues of arene or heteroarene monomers and dibenzosilole monomers. In any of the polymerization methods described herein, polymerizable monomers bearing one or more water-solubilizing groups can be used in the polymerization reaction to afford water-soluble dibenzosilole polymers and copolymers.

Figure 5H:
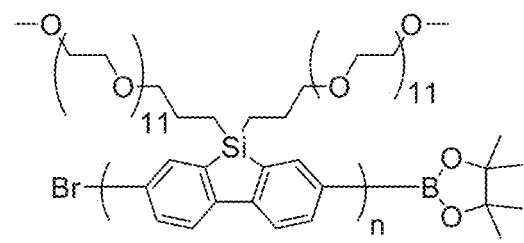
FIG. 5H is a representative dibenzosilole polymer that can be prepared by a Suzuki coupling reaction between dibromide substituted and diboronate substitute monomers.
Figure 5I:
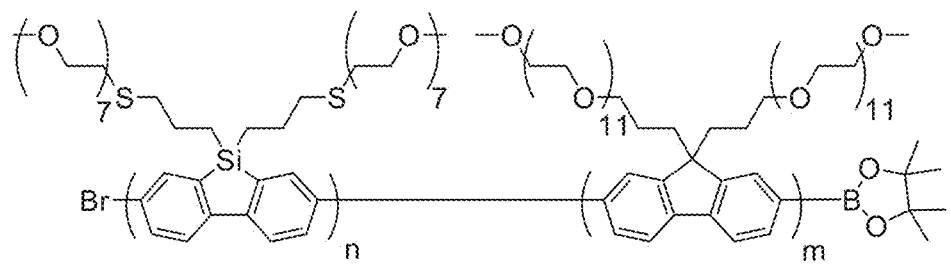
FIG. 5I is a representative dibenzosilole polymer that can be prepared by a Suzuki coupling reaction between dibromide substituted and diboronate substitute monomers.
Figure 5J:
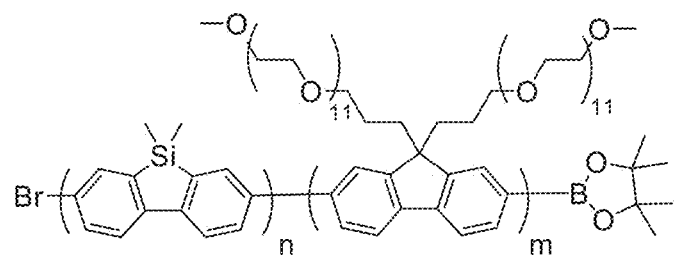
FIG. 5J is a representative dibenzosilole polymer that can be prepared by a Suzuki coupling reaction between dibromide substituted and diboronate substitute monomers.
Figure 5K:
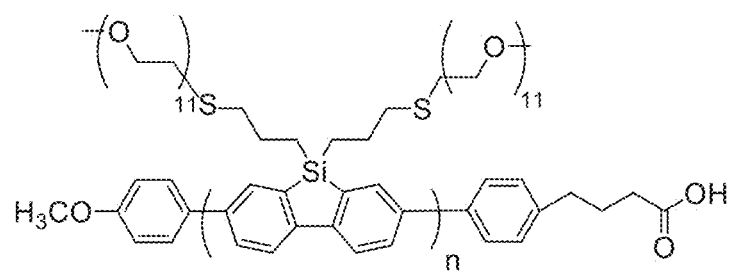
FIG. 5K is a representative dibenzosilole polymer bearing a reactive end group.
Figure 5L:
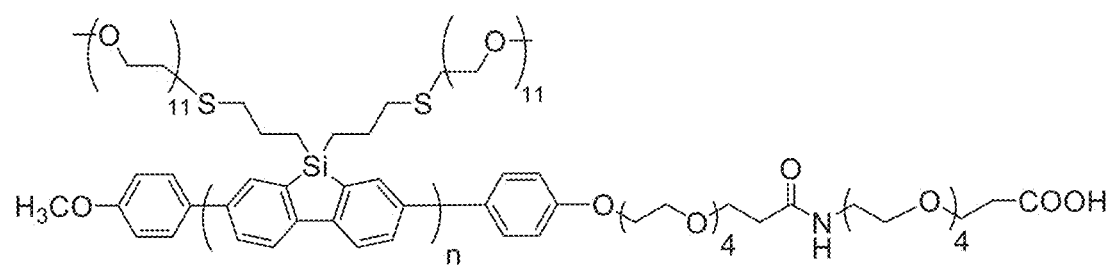
FIG. 5L is a representative dibenzosilole polymer bearing a reactive end group.
Figure 5M:
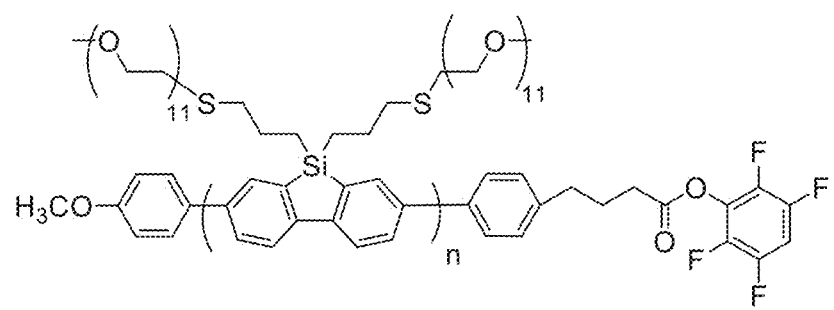
FIG. 5M is a representative dibenzosilole polymer bearing a reactive end group.
Figure 5N:
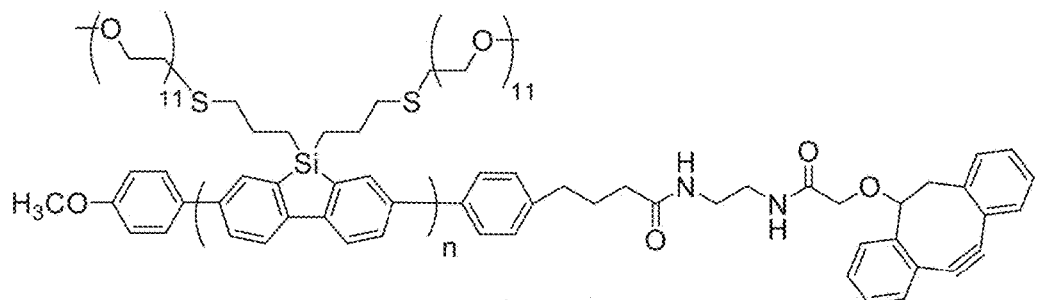
FIG. 5N is a representative dibenzosilole polymer bearing a reactive end group.
Figure 5O:
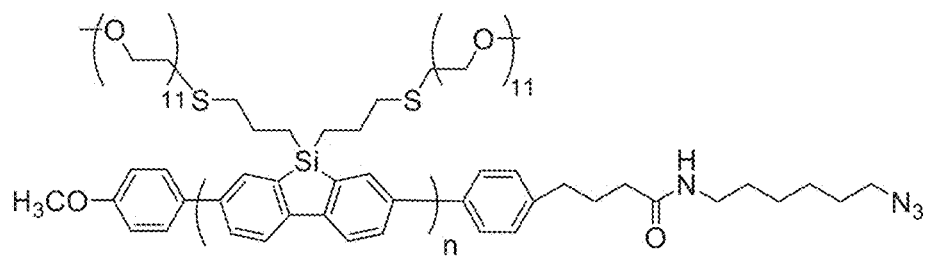
FIG. 5O is a representative example of a dibenzosilole polymer bearing a reactive end group.
Figure 5P:
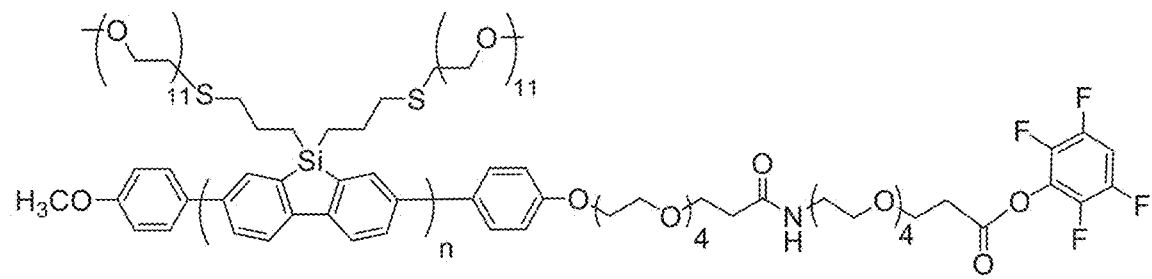
FIG. 5P is a representative dibenzosilole polymer bearing a reactive end group.
Figure 5Q:
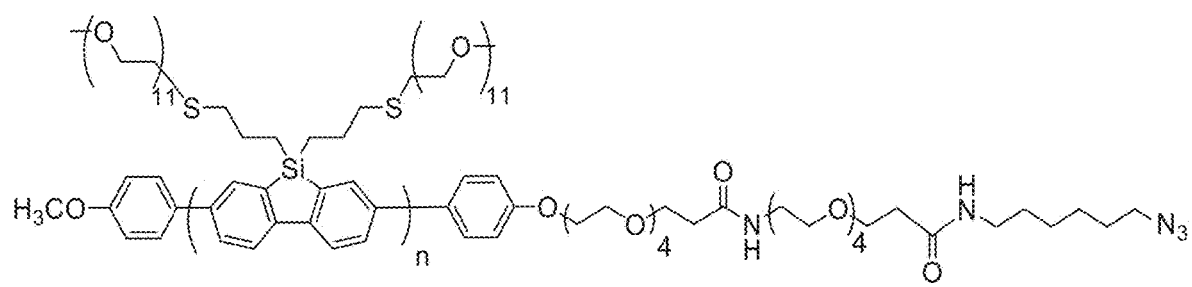
FIG. 5Q is a representative dibenzosilole polymer bearing a reactive end group.
Figure 5R:
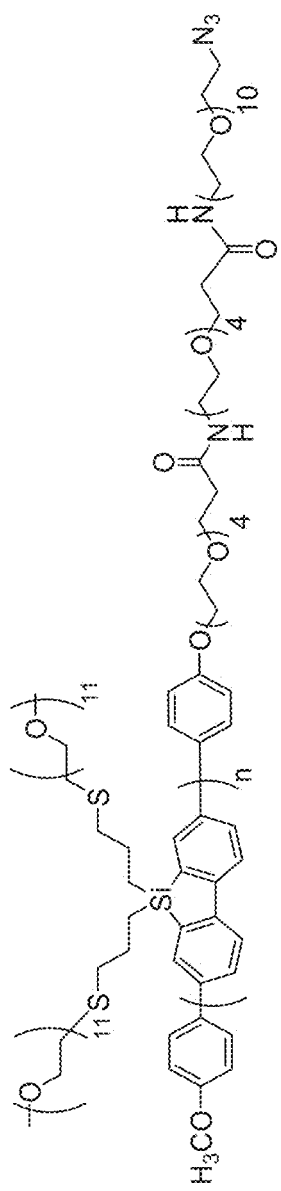
FIG. 5R is a representative dibenzosilole polymer bearing a reactive end group.
Figure 5S:
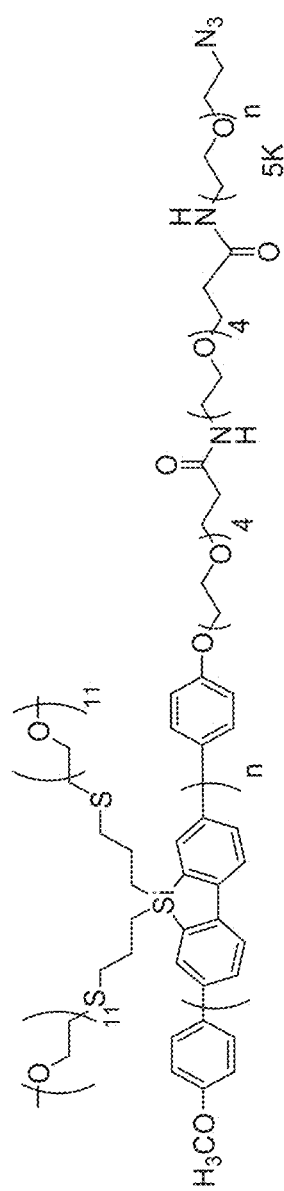
FIG. 5S is a representative dibenzosilole polymer bearing a reactive end group.
Figure 5T:
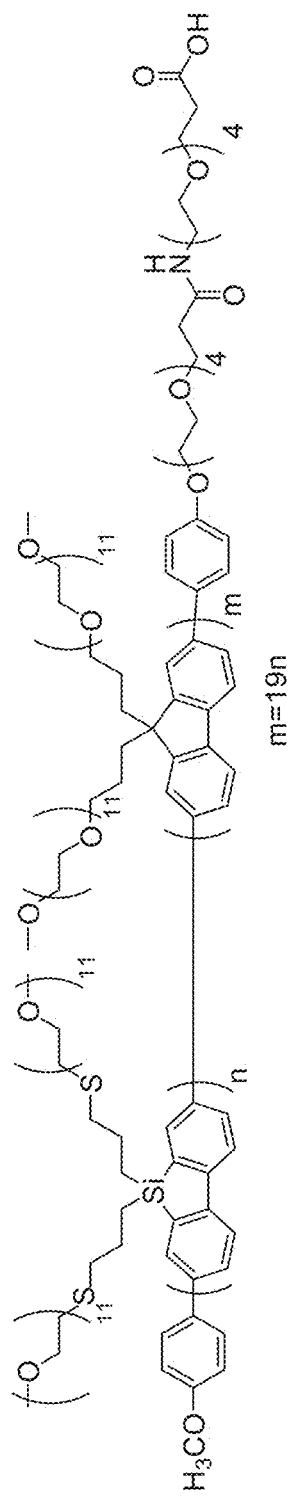
FIG. 5T is a representative dibenzosilole polymer bearing a reactive end group.
Figure 5U:
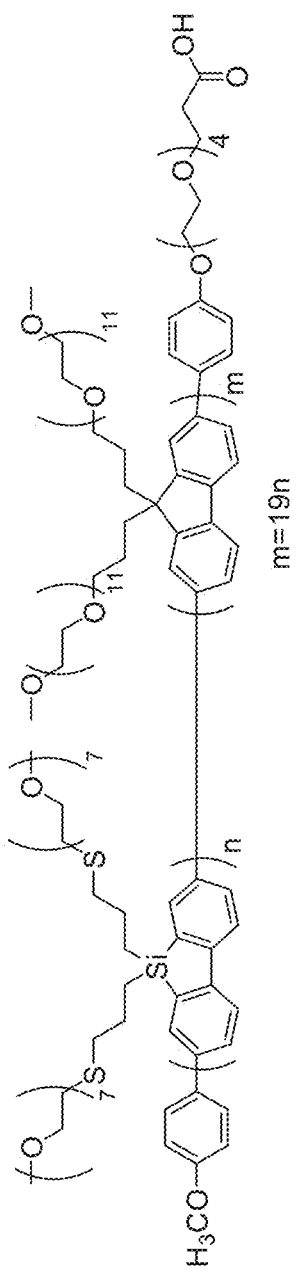
FIG. 5U is a representative dibenzosilole polymer bearing a reactive end group.
Figure 5V:
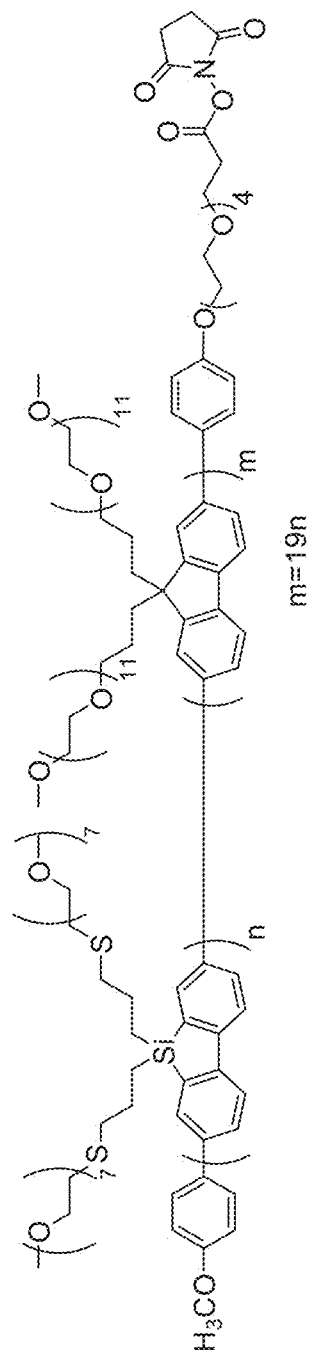
FIG. 5V is a representative dibenzosilole polymer bearing a reactive end group.

Polymers produced using the described methods can include one or more dibenzosilole monomer residues. The polymer can be a homopolymer formed by polymerization of a plurality of dibenzosilole monomers residues or a copolymer formed by polymerization of a plurality of dibenzosilole and aromatic monomers residues. The polymer can include blocks of dibenzosilole and/or aromatic monomer residues to form a block copolymer. Alternatively, the dibenzosilole and/or aromatic monomer residues can be incorporated into the polymer randomly or in an alternating sequence. Representative examples of dibenzosilole homopolymers and copolymers that can be prepared by a Suzuki coupling reaction between dibromide substituted and diboronate substitute monomers include those represented by the structures shown in FIG. 5H-5J. The total number of dibenzosilole monomer residues (n) and aromatic monomers (m), in the case of a copolymer, can vary. The numbers n and m can be estimated based on the average molecular weight of the polymer. In some cases n and/or m may not be a whole number. Typically, n and m are independently about 1 to about 100. In some embodiments, n and m are independently 2 to about 50.

Polymers bearing bromide and boronate end groups can be further capped with a desired group (e.g., by Suzuki coupling reaction). The end cap can introduce a reactive functional group that can be used, for example, as an attachment site for a conjugated substance as described here. Representative reactive groups include carboxylic acid, succinimidyl ester, maleimide, amine, azide, and alkyne groups. The reactive functional group can be used for the attachment of a substance (e.g., protein or nucleic acid) to form a conjugate. For example, a dibenzosilole polymer can be capped with a reactive group, such as a carboxylic acid functional group, that can be coupled to an antibody. Representative examples of dibenzosilole polymers bearing reactive end groups include those represented by the structures shown in FIG. 5K-5V, where n and m are as described above.

Hydrophilic dibenzosilole polymers provided herein can be used in applications that are conducted in aqueous systems. Such dibenzosilole compounds herein can be used in a biological assay, for example, as fluorescent probes in cell imaging and cell sorting, in flow cytometry, as biological and chemical sensors, in hybridization assays (e.g., FISH), PCR assays, immunoassays such as ELISA and Western blotting.

Thus, also provided are methods to determine the presence of target molecule in a sample. Generally, the method involves providing a solution of dibenzosilole polymer and then treating a sample (e.g., a biological material or cells) that contains or is thought to contain target molecules within the solution. For biological assays, the polymer is typically provided in a biologically compatible solution. The sample can be any material that contains a target molecule or is suspected of containing a target molecule and can contain materials of biological or synthetic origin. The target molecule can be free in solution or contained with a biological material, such as a cell. Exemplary target molecules include, without limitation, proteins (e.g., antibodies or antigens), polysaccharides, lipids, nucleic acids, biotin, streptavidin, and the like. Representative examples of samples include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, in vitro cell culture constituents, and recombinant libraries of polynucleotide sequences.

The methods described herein can utilize live cells, dead or fixed cells or a combination of live and dead cells. For labeling of living cells, the dibenzosilole polymer is added to a sample that contains living cells. The sample can include cells suspended in a buffer or media, or cells adherent to a glass or plastic surface, or bathed in a buffer or media. Alternatively, or in addition, the sample can include cells that have been be lysed or permeabilized to release the cellular components (e.g., proteins, nucleic acid polymers, nucleotides or nucleosides) from within the cells. Cells can be treated with a cell fixative reagent, or a cell fixative reagent combined with a cell permeabilizing reagent, or a cell permeabilizing reagent. The sample can include eukaryotic cells, prokaryotic cells, biological fluids, isolated cell nuclei, or tissue. The cells may be suspended in a fluid (e.g., a biological fluid or an aqueous fluid, such as buffer or water) or may be in a solid form, such as cells adherent to plates, coverslips, dishes, flasks, or solid tissue samples that have been disaggregated.

The dibenzosilole polymer can be used in an unbound form or can be linked to an affinity molecule to provide a composition that can associate with the target molecule under appropriate conditions. The association can be achieved by covalent or non-covalent bonding of the composition to the target molecule. The affinity molecule can recognize and bind to the target molecule through non-covalent interactions (e.g., hydrogen bonding, van der Waals force, and the like), or the polymer can include a reactive group that is capable of binding covalently to the target molecule. Representative examples of affinity molecules include biomolecules, such as proteins (e.g., antibody or antigen), nucleic acids, biotin, and avidin and derivatives thereof (e.g., streptavidin), and the like.

In certain embodiments, polymer can bear a reactive group that can react with a complementary reactive group on the target molecule to provide a covalent linkage between the polymer and the target molecule. Various types of reactions can be utilized to couple a reactive dibenzosilole derivative to a target molecule, including, for example, various types of click reactions (e.g., [3+2] cycloadditions, such as the Huisgen 1,3-dipolar cycloaddition and Diels-Alder reactions). For example, the polymer can bear a reactive pendant group (e.g., an azide or alkyne) that can react via a click reaction with a complementary reactive group (e.g., an alkyne or azide) on the target molecule to bind the polymer to the target molecule. The alkyne can be a branched or unbranched hydrocarbon group containing at least one —C≡C— triple bond and can be optionally substituted at one or more positions. Substituents on substituted alkynyl groups include, for example, hydroxyl, cyano, alkoxy, =O, =S, —NO$_2$, halogen, haloalkyl, heteroalkyl, amine, thioether and —SH. In certain embodiments, the alkyne group is a terminal alkyne. Examples of terminal alkynyl groups include ethynyl, n-propynyl, isopropynyl, propargyl, octynyl, decynyl and the like. In other embodiments, the alkyne is a cyclic alkyne. In certain embodiments, the cyclic alkyne is a cyclooctyne. Representative cyclooctynes include monocyclic or bicyclic or tricyclic, unsubstituted or substituted cyclooctynes including, for example, monofluorinated cyclooctynes and difluorinated cyclooctynes. In certain embodiments, the cyclic alkyne is a cyclooctyne, monoarylcyclooctyne, or diarylcyclooctyne, such as a dibenzocyclooctyne (DIBO). Use of a strained cyclooctyne as the reactive group can facilitate a click cycloaddition reaction in the absence of a metal catalyst (e.g., copper), such as when using living cells or delicate fluorescent proteins and antigens.

Thus, in yet another embodiment, dibenzosilole polymers provided herein can include a cyclic alkyne group, such as DIBO or a DIBO derivative. DIBO-containing polymers can be conjugated to a complementary azide-containing molecule such as streptavidin-azide or azide-derivatized primary antibodies. Antibodies site-specifically modified at an Fc-glycan can be prepared using the SiteClick™ labeling products available from Life Technologies Corporation (Carlsbad, Calif.). For some applications, it can be advantageous to remove unreacted DIBO-derivatized polymer from a reaction mixture. In such applications, azide-derivatized resins can be used to remove excess polymer from conjugation mixtures.

The sample can be contacted with the polymer composition under conditions and for a time sufficient to allow the polymer composition to associate with or bind to the target molecule, if present, using methods that are known to those skilled in the art. The polymer is typically present in a concentration sufficient to yield a detectable optical response under the desired conditions. The method can further include an optional washing step using methods known to those skilled in the art to remove unbound polymer and other reagents from the polymer-bound target molecule.

At any time after or during treatment of the sample with the polymer, the sample is illuminated with a wavelength of light selected to give a detectable optical response, and observed with a means for detecting the optical response. For example, after sufficient time for the polymer to complex with target molecules in the sample, the sample is excited with a light source (e.g., a laser). Due to its optical properties, the polymer can emit a fluorescence signal upon excitation at an appropriate wavelength of light. Preferably, the light source provides photons of a wavelength that fall within the absorption wavelength range of the compound (e.g., 350-450 nm). Any suitable instrument and technique known to those skilled in the art can be used to excite the dibenzosilole polymer and detect the emitted light. Equipment that is useful for illuminating dibenzosilole polymers includes, but is not limited to, hand-held ultraviolet lamps, mercury arc lamps, xenon lamps, lasers and laser diodes. These illumination sources are optionally integrated into flow cytometers, laser scanners, fluorescence microplate readers, fluorometers, or chromatographic detectors. Certain polymers provided herein are excitable at or near wavelengths in regions that closely match the output of standard equipment. For example, for flow cytometry and imaging experiments, it is common to excite the sample using a violet laser (e.g., ~405 nm).

Detection of the light emitted from the polymer indicates the presence of the target molecule in the sample. The optical response can be detected by visual inspection, or by devices such as CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is analyzed using a flow cytometer, examination of the sample, optionally, can further include sorting portions of the sample according to their fluorescence response. Methods for detecting the presence of target molecules in a sample can further include quantification of the detected target molecules.

In certain embodiments, detection of target molecules in a sample can be accomplished using flow cytometry analysis or imaging. For flow cytometry assays, the polymer can be added to the buffer or media containing living cells, incubated, and data acquired without washing the dye out of the sample. To ensure analysis is performed on living cells, a dead cell dye or a live cell dye can be included in the testing for gating out of dead cells or gating on living cells. For imaging, the polymer is combined with a sample (e.g., a biological fluid or a sample of cells) that contains or is thought to contain target molecules to form a mixture. The solution is incubated for a sufficient amount of time for the compound to associate with the target molecule in the sample (about 5 minutes to 15 minutes to one hour or more). The incubated sample is then illuminated with an appropriate wavelength of light to generate a detectable optical response resulting from the presence of a complex of the compound with a nucleic acid molecule in the sample. Illumination may be achieved by the use of a laser diode laser, mercury arc lamp or other such focused light source. The optical response can be detected to determine presence and location of target molecules in the sample and may be achieved using detection methods well known to those skilled in the art. Detection may be achieved by imaging to determine the presence and location of target molecules in a sample. Additional applications of the disclosed fluorescent compounds include labeling of particles and bare nuclei. In one embodiment, labeled particles and nuclei can be used for instrument set-up and calibration purposes (e.g., set-up and calibration of an instrument).

In certain methods, dibenzosilole polymers provided herein can be used to label cells (e.g., flow cytommetry or cell imaging experiments). The method can include contacting a cell with the polymer or a conjugate thereof for a time sufficient to allow the polymer or conjugate to bind to the surface of the cell or enter into the cell. In certain methods, the affinity molecule (e.g., an antibody) can bind to a target molecule (e.g., cell surface protein) on the surface of the cell. Thus, also provided herein is a cell that includes a dibenzosilole polymer or conjugate. The polymer or conjugate can reside within the cytoplasm or nucleus of the cell, on or within a portion of the cell membrane, or is associated with the surface of the cell.

Compounds disclosed herein can be incorporated into kits that facilitate the practice of various assays. For example, kits are provided for use in biological experiments (e.g., cell imaging and flow cytometry). The kits can be packaged with the compound in a dry form or with the compound in solution. The kits can optionally further include one or more buffering agents, typically present as an aqueous solution, sample preparation reagents, additional detection reagents, organic solvent, other fluorescent detection probes, standards, microspheres, specific cell lines, antibodies and/or instructions for carrying out an assay. Additional optional agents include components for testing of other cell functions in conjunction with the compound. Also provided is a kit for labeling cells that includes a conjugate of a dibenzosilole polymer and an affinity molecule that is capable of binding to a target molecule located in a cell, within a portion of the extracellular membrane or on the surface of a cell; and instructions for labeling the cell and detecting the conjugate labeled cell.

The following examples are included to demonstrate certain embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

The examples provided herein utilize the following general methods unless indicated otherwise. $^1$H NMR spectra were recorded on a Bruker 400 MHz instrument using $CDCl_3$. The photophysical properties were characterized by electronic absorption and fluorescence spectra in aqueous solution. UV-Vis spectra and molar extinction coefficients were measured using a PerkinElmer LAMBDA 35 Spectrophotometer. Fluorescence spectra were recorded on a LS 45 Fluorescence Spectrometer. Fluorescent quantum yields were measured using a Hamamatsu PL quantum yield measurement system. Gel permeation chromatography (GPC) was carried out in THF at 50° C. using a 5 μm Waters Styragel® HR3 and a HR4 GPC column system on a Waters 2960 Alliance HPLC Separations Module with a Waters 2996 PDA Detector using a flow rate of 0.5 mL/min. The system was calibrated with polystyrene standards in the range of 3500 to 200,000 g/mol (Sigma-Aldrich). Reagents and solvents were used as obtained from commercial suppliers except where indicated otherwise.

Example 1

2,5,8,11,14,17,20,23,26,29,32-Undecaoxatetratriacontan-34-yl-4-methylbenzenesulfonate

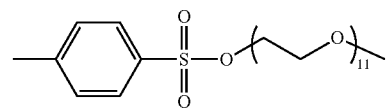

(1)

A small portion of sodium hydride (1.8 g, 45.5 mmol) was added to a solution of 2,5,8,11,14,17,20,23,26,29,32-undecaoxate-tratriacontan-34-ol, (18 g, 34.9 mmol, ChemPep Inc.) in dry THF (60 mL) over 10 min while the reaction mixture was cooled in an ice-water bath and stirred for 2 h. 4-methylbenzene-1-sulfonyl chloride (10 g, 52.5 mmol) was added, and the reaction mixture was stirred at room temperature overnight. The resulting solid was filtered off, and the filtrate was concentrated under vacuum. The crude product was purified by column chromatography over silica gel eluting with 2% methanol in chloroform to yield product (1) (19.3 g, 82% yield). $^1$H NMR (400 MHz, $CDCl_3$) δ 7.83 (d, 2H), 7.37 (d, 2H), 4.18 (t, 2H), 3.72-3.57 (m, 42H), 3.40 (s, 3H), 2.47 (s, 3H).

Example 2

S-2,5,8,11,14,17,20,23,26,29,32-Undecaoxatetratriacontan-34-yl ethanethioate

(2)

A mixture of 2,5,8,11,14,17,20,23,26,29,32-undecaoxa-tetratriacontan-34-yl 4-methyl-benzenesulfonate (1) (10 g, 14.9 mmol) and potassium thioacetate (10.2 g, 89.6 mmol) in dry acetonitrile (120 mL) was heated at 90° C. for 2 h. The reaction mixture was cooled to room temperature and solvent removed under vacuum. Chloroform (150 mL) was added to the resulting residue, and the mixture stirred at room temperature for 10 min. The resulting solid was removed by filtration, and the filtrate was concentrated under vacuum. The crude product was purified by column chromatography over silica gel eluting with 4% water in acetonitrile to yield product (2) (7.2 g, 83% yield). $^1$H NMR (400 MHz, CDCl$_3$) δ 3.67-3.61 (m, 42H), 3.40 (s, 3H), 3.11 (t, 2H), 2.36 (s, 3H).

Example 3

2,5,8,11,14,17,20,23,26,29,32-Undecaoxatetratria-contane-34-thiol

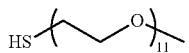
(3)

Figure 7:
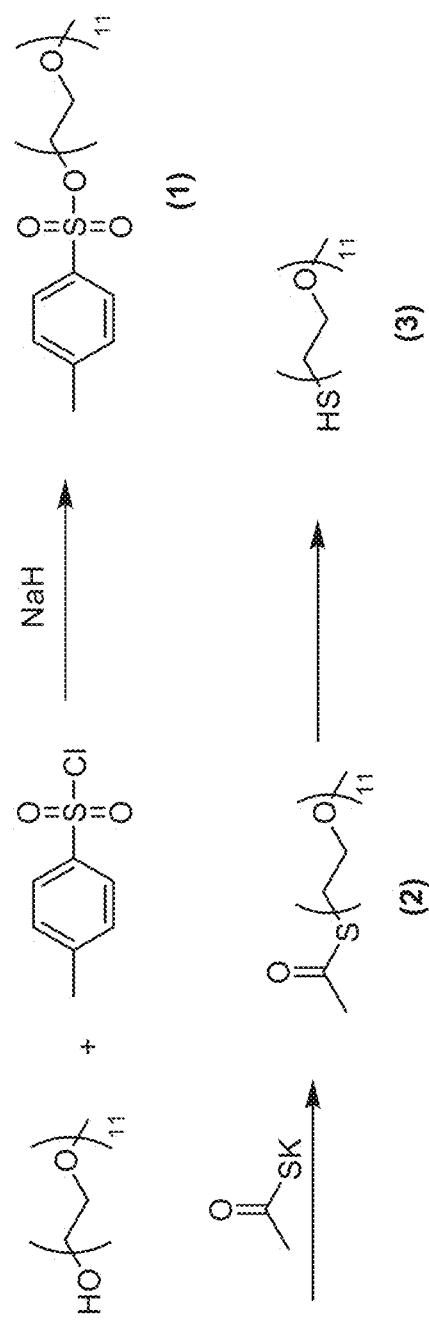
FIG. 7 is a reaction scheme for the preparation of Compound (3) from compounds (1) and (2).

The synthetic scheme for the preparation of Compound (3) from compounds (1) and (2) is depicted in FIG. 7. HCl (36%, 10 mL) was added to a solution of S-2,5,8,11,14,17,20,23,26,29,32-undecaoxatetratriacontan-34-yl ethanethio-ate (2) (7 g, 2.0 mmol) in methanol (100 mL). The solution was stirred at room temperature for 48 h and then concentrated under vacuum. The resulting crude product was purified by column chromatography eluting with 1% methanol in chloroform to yield product (3) as clear oil (6.0 g, 93% yield). $^1$H NMR (400 MHz, CDCl$_3$) δ 3.69-3.62 (m, 40H), 3.58-3.55 (m, 2H), 3.40 (s, 3H), 2.72 (q, 2H).

Example 4

5,5-Diallyl-3,7-dibromo-5H-dibenzo[b,d]silole

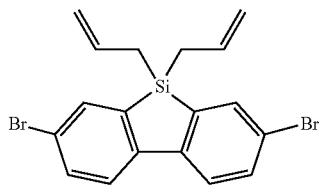
(4)

n-Butyllithium (1.6 M in hexane, 11.1 mL, 17.8 mmol) was added dropwise over 15 min to a solution of 4,4'-dibromo-2,2'-diiodo-1,1'-biphenyl (2.0 g, 3.56 mmol) (prepared according to the protocol reported in Chan, K. L.; McKiernan, M. J.; Towns, C. R.; Holmes, A. B. J. Am. Chem. Soc. 2005, 127, 7662) in anhydrous THF (20 mL) while the reaction mixture was stirred in a dry ice-acetone bath under Ar atmosphere. After stirring the reaction mixture for an additional 1.5 h, diallyldichlorosilane (1.4 mL, 8.2 mmol, Gelest Inc.) was added and stirred for additional 1.5 h at room temperature. The reaction mixture was quenched with water (2 mL), and the solvent was removed under vacuum. The crude product was then dissolved in chloroform (100 mL) and the organic layer was washed with brine, dried over anhydrous Na$_2$SO$_4$, filtered and evaporated. The crude material was purified column chromatography over silica gel eluting with hexanes to yield product (4) as white solid (0.81 g, 54% yield). $^1$H NMR (400 MHz, CDCl$_3$) δ 7.67 (s, 2H), 7.64 (d, 2H), 7.59 (d, 2H), 5.83 (h, 2H), 5.0 (d, 4H), 1.85 (d, 4H).

Example 5

3,7-Dibromo-5,5-di(2,5,8,11,14,17,20,23,26,29,32-undecaoxa-35-thiaoctatriacontan-38-yl)-5H-dibenzo[b,d]silole

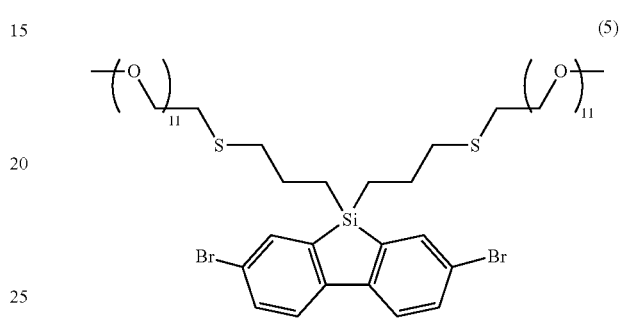
(5)

A solution of 5,5-diallyl-3,7-dibromo-5H-dibenzo[b,d]silole (4) (100 mg, 0.24 mmol), 2,5,8,11,14,17,20,23,26,29,32-undecaoxatetratriacontane-34-thiol (3) (380 mg, 0.71 mmol) and 2,2-dimethoxy-2-phenyl-acetophenone (26 mg, 0.10 mmole) in THF (BHT free, 4.5 mL) was prepared in a quartz flask equipped with a condenser and illuminated (photolysis) with BLAK-RAY long wavelength UV light under Ar atmosphere for 2 h. The photolysis reaction mixture was concentrated under vacuum, and the resulting crude product was purified by column chromatography over silica gel eluting with 5% methanol in chloroform to yield product (5) (270 mg, 76% yield). $^1$H NMR (400 MHz, CDCl$_3$) δ 7.67 (s, 2H), 7.64 (d, 2H), 7.59 (d, 2H), 5.83 (h, 2H), 5.0 (d, 4H), 1.85 (d, 4H).

Example 6

5,5-Di(2,5,8,11,14,17,20,23,26,29,32-undecaoxa-35-thiaoctatriacontan-38-yl)-3,7-bis(4,4,5,5-tetramethyl-1,3,2-dioxaborolan-2-yl)-5H-dibenzo[b,d]silole

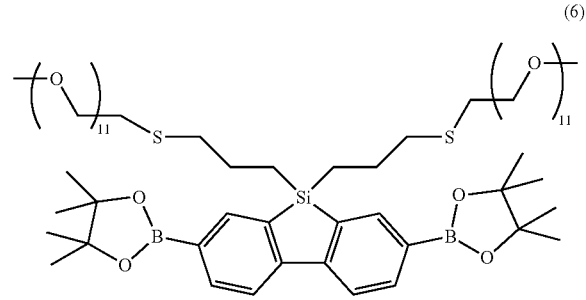
(6)

Figure 8:
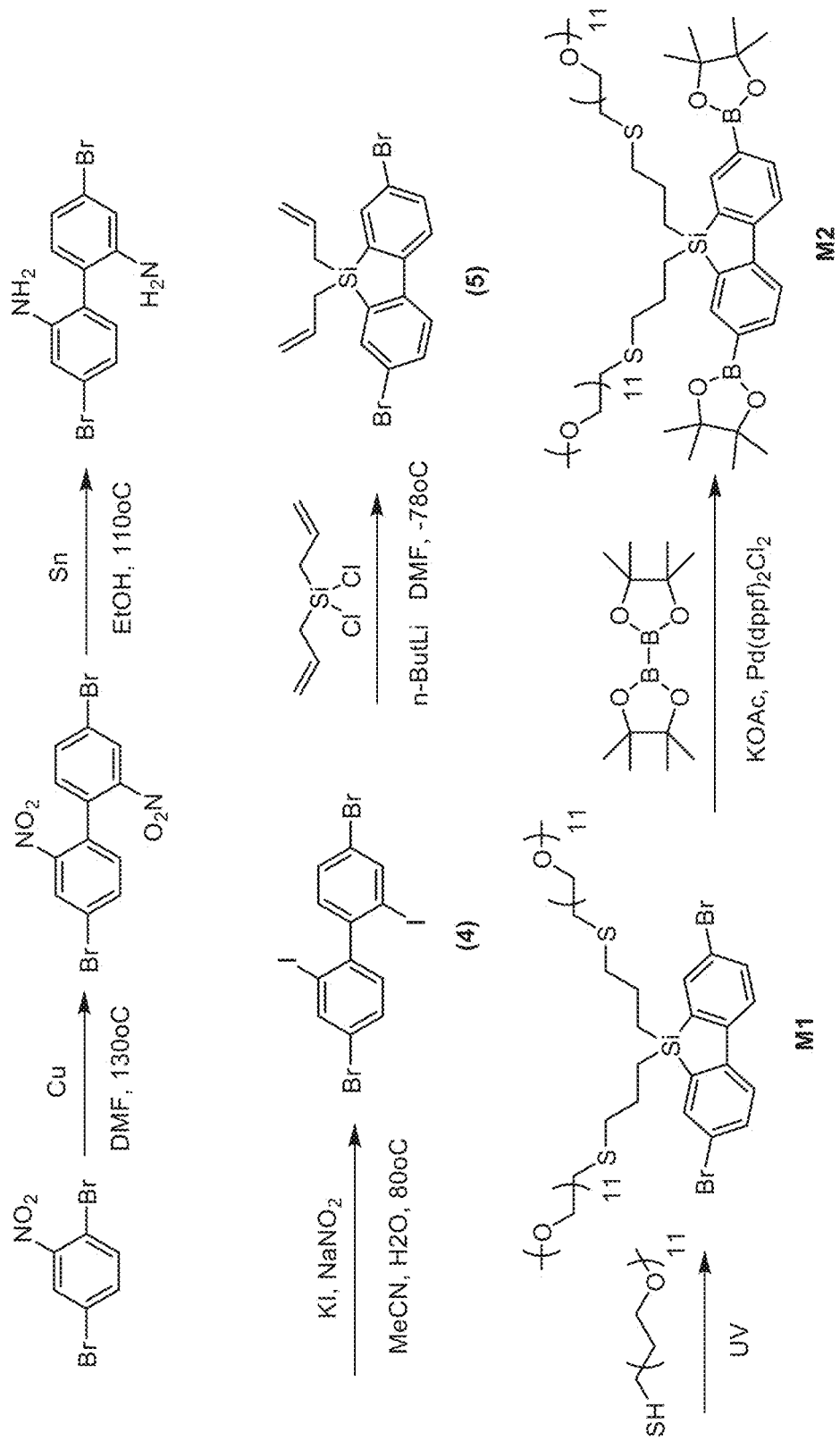
FIG. 8 is a reaction scheme for the preparation of Compound (6).

The synthetic scheme for the preparation of Compound (6) from compounds (4) and (5) is depicted in FIG. 8. A mixture of 3,7-dibromo-5,5-di(2,5,8,11,14,17,20,23,26,29,32-undecaoxa-35-thiaoctatriacontan-38-yl)-5H-dibenzo[b,d]silole (5) (500 mg, 0.34 mmol), bis (pinacolato)diboron (190 mg, 0.75 mmol), [1,1'-bis(diphenylphosphino) ferrocene]dichloropalladium(II) (97 mg, 0.12 mmol) and potassium acetate (200 mg, 2.0 mmol) in anhydrous dioxane (12 mL) was heated under reflux for 3 h under Ar atmosphere. After the reaction mixture was cooled down to room temperature, the solid was removed by filtration, and the filtrate was concentrated under vacuum. The resulting crude product was purified by column chromatography eluting with 10% methanol in dichloromethane to give product (6) as oil (220 mg, 41% yield). $^1$H NMR (400 MHz, CDCl$_3$) δ 7.69 (s, 2H), 7.65 (d, 2H), 7.57 (d, 2H), 3.67-3.53 (m, 84H), 3.39 (s, 6H), 2.59 (t, 4H), 2.46 (4H), 1.57-1.55 (m, 4H), 1.11-1.07 (m, 4H).

Example 7

3,7-Dibromo-5,5-di(2,5,8,11,14,17,20-heptaoxa-23-thiahexacosan-26-yl)-5H-dibenzo[b,d]silole

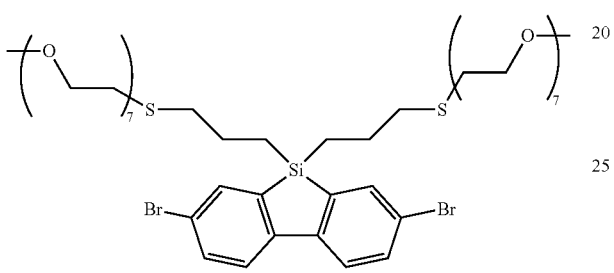

(7)

Compound (7) was prepared in a similar method as described in Example 5, with an exception that 2,5,8,11,14,17,20,23-octaoxapentacosane-25-thiol was used.

Example 8 tert-Butyl 1-(tosyloxy)-3,6,9,12-tetraoxapentadecan-15-oate

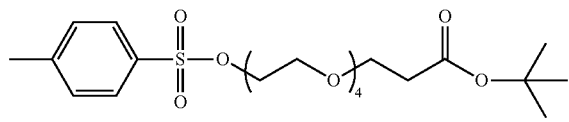

(8)

4-methylbenzene-1-sulfonyl chloride (975 mg, 5.12 mmol) was added to a solution of tert-butyl 1-hydroxy-3,6,9,12-tetraoxapentadecan-15-oate (1 g, 3.10 mmol) and triethylamine (4.0 mL, 29.0 mmol) in dichloromethane (20 mL) chilled in an ice-water bath. The mixture was stirred overnight at room temperature and then concentrated under vacuum. The resulting crude product was purified by column chromatography over silica gel eluting with ethyl acetate and hexane (1:1) to yield product (8) as clear oil (1.41 g, 97% yield).

Example 9 tert-Butyl 1-(4-bromophenoxy)-3,6,9,12-tetraoxapentadecan-15-oate

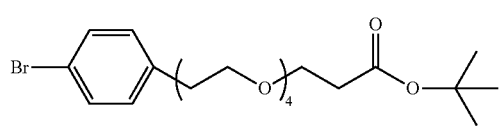

(9)

A mixture of 4-bromophenol (620 mg, 3.55 mmol), tert-butyl 1-(tosyloxy)-3,6,9,12-tetraoxapentadecan-15-oate (1.41 g, 2.96 mmol) and potassium carbonate (612 mg, 4.44 mmol) in DMF (15 mL) was stirred at ~70° C. for 4 h. The solvent was removed under vacuum, and the resulting residue was purified by column chromatography yielding product (9) as clear oil (1.31 g, 92% yield).

Example 10

1-(4-Bromophenoxy)-3,6,9,12-tetraoxapentadecan-15-oic Acid

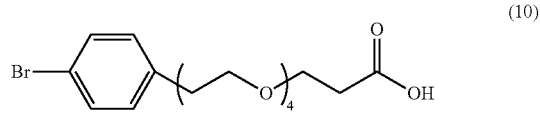

(10)

A solution of tert-butyl 1-(4-bromophenoxy)-3,6,9,12-tetraoxapentadecan-15-oate (9) (1.40 g, 2.93 mmol) and trifluoroacetic acid (2.5 mL, 33 mmol) in dichloromethane (15 mL) was stirred at room temperature for 5 h and then concentrated under vacuum to give a product (10) (1.11 g, 90% yield).

Example 11

2,5-Dioxopyrrolidin-1-yl 1-(4-bromophenoxy)-3,6,9,12-tetraoxapentadecan-15-oate

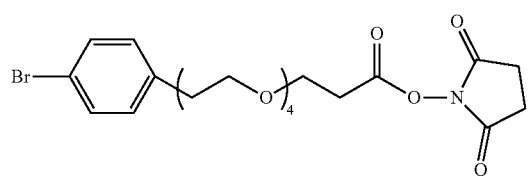

(11)

A solution of 1-(4-bromophenoxy)-3,6,9,12-tetraoxapentadecan-15-oic acid (10) (510 mg, 1.21 mmol) and dry pyridine (290 uL, 3.63 mmol) was prepared in dry tetrahydrofuran (5 mL). Solid succinimidyl trifluoroacetate (640 mg, 3.02 mmol) was added to the solution. After the reaction mixture was stirred for 2 hours, dichloromethane (50 mL) was added. The mixture was washed with HCl solution (0.1 N, 2×25 mL) and water (30 mL). The organic layer was separated, dried over Na$_2$SO$_4$ and filtered to yield product (11).

Example 12

1-(4-Bromophenoxy)-15-oxo-3,6,9,12,19,22,25,28-octaoxa-16-azahentriacontan-31-oic Acid

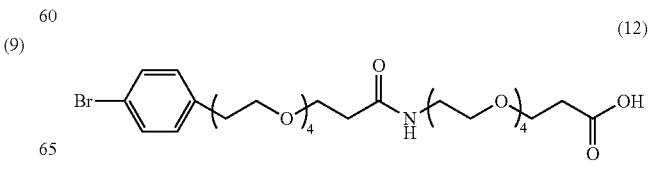

(12)

The filtrate prepared in Example 10 was concentrated to about 20 mL, dry pyridine (100 uL, 1.24 mmol) was added followed by addition of 1-amino-3,6,9,12-tetraoxapentadecan-15-oic acid (328 mg, 1.24 mmol). The reaction mixture was stirred at room temperature for 2 h and then concentrated under vacuum to give a crude product, which was purified by column chromatography over silica gel eluting with 5% methanol in chloroform to give product (12) (504 mg, 62% yield).

Example 13

Poly(2,7-dibenzosilole)-PEG11 Analogue

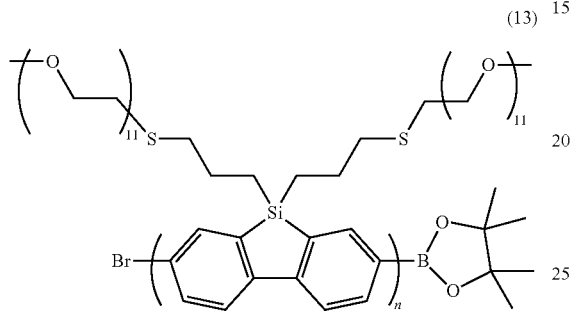

(13)

3,7-dibromo-5,5-di(2,5,8,11,14,17,20,23,26,29,32-undecaoxa-35-thiaoctatriacontan-38-yl)-5H-dibenzo[b,d]silole (5) (155 mg, 0.105 mmol), 5,5-di(2,5,8,11,14,17,20,23,26,29,32-undecaoxa-35-thiaoctatriacontan-38-yl)-3,7-bis(4,4,5,5-tetramethyl-1,3,2-dioxaborolan-2-yl)-5H-dibenzo[b,d]silole (6) (165 mg, 0.105 mmol) and tetrakis(triphenylphosphine)palladium(0) (36 mg, 0.03 mmol) were mixed and dissolved in 0.5 mL tetrahydrofuran in a 15 mL round-bottom flask equipped with a condenser and vacuum adaptor. 0.3 mL of 2M sodium carbonate solution was added and the flask was connected to a Schlenk line. The reagent mixture was carefully degassed through 4 cycles of freeze-pump-thaw and after the last cycle the flask was refilled with argon. The reaction mixture was heated at 80° C. with vigorous stirring under argon. After 24 h, the reaction was stopped and cooled to room temperature. The organic layer was carefully collected, evaporated to dryness and redissolved in 4 mL chloroform. The solution was filtered through 0.45 μm glass fiber filter and then poured into 60 mL hexane to precipitate the polymers. Polymers were collected by centrifugation and redissolved in chloroform. The precipitation-centrifugation-redissolution cycle was repeated twice more. The crude polymer product was then dissolved in 10 mL DI water and filtered 3 times through Amicon® Ultra-4 Centrifugal Filter Units (MWCO, 30K) (available from EMD Millipore Corporation, Billerica, Mass.) to remove low molecular weight polymers. The polymer product (n=27) was dried in reduced pressure and collected as amber wax (190 mg; 60%).

Gel permeation chromatography (GPC) was carried out in THF at 50° C. using a 5 μm Waters Styragel® HR3 and a HR4 GPC column system on a Waters 2960 Alliance HPLC Separations Module with a Waters 2996 PDA Detector (available from Waters Corporation, Milford, Mass.) using a flow rate of 0.5 mL/min. The system was calibrated with polystyrene standards in range of 3500 to 200,000 g/mol (Sigma-Aldrich). GPC ($M_w$=42,000 g/mol, $M_n$=36,000; PDI=1.2).

Example 14

C4-COOH Derivative of Poly(2,7-dibenzosilole)-PEG11 Analogue

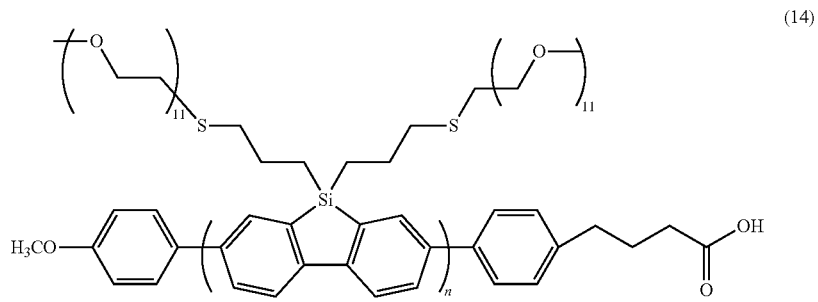

(14)

4-(4-iodophenyl)butanoic acid (42 mg, 0.10 mmol) was mixed with polymer (13) (130 mg, 0.10 mmol) obtained in Example 13 and tetrakis(triphenylphosphine)palladium(0) (5 mg, 0.0043 mmol), and the mixture was dissolved in 0.9 mL THF. 0.6 mL of 2M sodium carbonate solution was added. The reaction mixture was degassed through 3 cycles of freeze-pump-thaw and then heated overnight at 80° C. under nitrogen. The organic layer was carefully collected, evaporated to dryness and redissolved in 4 mL chloroform. The solution was filtered through 0.45 μm glass fiber filter and then poured into 60 mL hexane to precipitate the polymers. Polymers were collected by centrifugation and redissolved in chloroform. The precipitation-centrifugation-redissolution cycle was repeated twice more. The crude polymer was then dissolved in 10 mL DI water and filtered through 0.45 μm glass fiber filter. The solution was washed 3 times with ethyl acetate and then evaporated under high pressure. The crude product was dissolved in 20% EtOH/80% H₂O and filtered 3 times through Amicon® Ultra-4 Centrifugal Filter Units (MWCO, 30K) to remove excessive reagents. The polymer product was dried under vacuum and collected as amber wax (125 mg; yield: 96%). The polymer was further end-capped using 4-methoxybenzenboronic acid (13 mg, 0.086 mmol) to yield terminal carboxylic acid capped polymer (14) (52 mg, yield: 47%).

Example 15

PEG8-COOH Derivative of Poly(2,7-dibenzosilole)-PEG11 Analogue

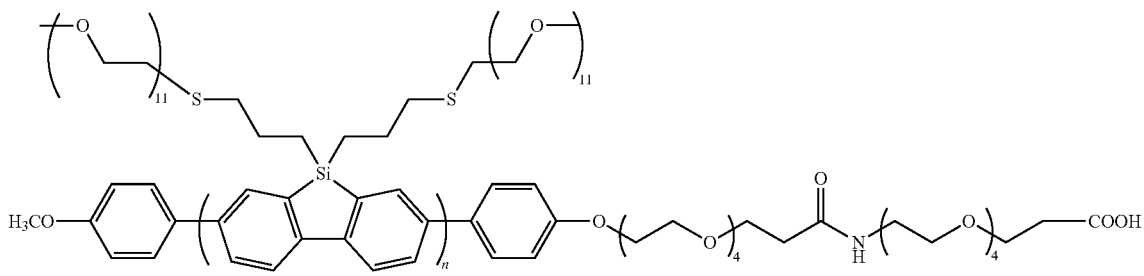

(15)

1-(4-bromophenoxy)-15-oxo-3,6,9,12,19,22,25,28-octaoxa-16-azahentriacontan-31-oic acid (12) (13 mg, 0.019 mmol) was mixed with the polymer (13) obtained in Example 13 (25 mg, 0.019 mmol) and tetrakis(triphenylphosphine)palladium(0) (6 mg, 0.0056 mmol), and the mixture was dissolved in 1.2 mL THF. 0.8 mL of 2M sodium carbonate solution was added. The reaction was degassed through 3 cycles of freeze-pump-thaw and then heated overnight at 80° C. under nitrogen. The organic layer was carefully collected, evaporated to dryness and redissolved in 2 mL chloroform. The solution was filtered through 0.45 µm glass fiber filter and then poured into 30 mL hexane to precipitate the polymers. Polymers were collected by centrifugation and redissolved in chloroform. The precipitation-centrifugation-redissolution cycle was repeated twice more. The crude polymer then was dissolved in 4 mL DI water and filtered through 0.45 µm glass fiber filter. The solution was washed with ethyl acetate three times, and then evaporated under high pressure. The crude product was dissolved in 20% EtOH/80% $H_2O$ and filtered 3 times through Amicon® Ultra-4 Centrifugal Filter Units (MWCO, 30K) to remove excessive reagents. The polymer product was dried in vacuum and collected as amber wax (23 mg; yield: 92%). The polymer was further end-capped using 4-methoxybenzenboronic acid (5 mg, 0.035 mmol) to yield terminal carboxylic acid capped polymer (15) (22.5 mg, yield: 98%).

Example 16

C4-TFP ester Derivative of Poly(2,7-dibenzosilole)-PEG11 Analogue

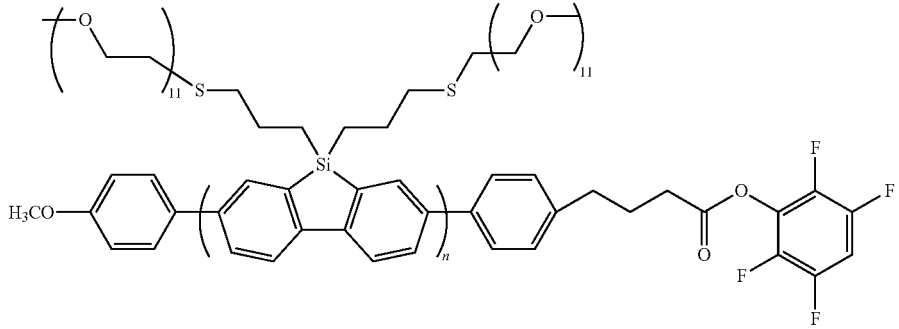

(16)

2,3,5,6-tetrafluorophenyl 2,2,2-trifluoroacetate (50 mL) and polymer (14) (25 mg, 0.019 mmol) obtained in Example 14 were dissolved in a dry 5 mL reaction vessel in 0.5 mL anhydrous pyridine. The reaction was stirred vigorously at room temperature for 30 min. The reaction mixture was filtered through 0.45 μm glass fiber filter and then poured into 10 mL hexane to precipitate the polymers. Polymers were collected by centrifugation and redissolved in chloroform. The precipitation-centrifugation-redissolution cycle was repeated one more time. The polymer was dissolved in 5 mL CHCl$_3$ and washed once with 1M HCl, then once with dilute NaHCO$_3$ solution and then once with saturated NaCl solution. The polymer product was dried over anhydrous MgSO$_4$ to evaporate all solvent yielding product (16) as amber wax (20 mg; 80%).

Example 17

DIBO Derivative of Poly(2,7-dibenzosilole)-PEG11 Analogue (17)

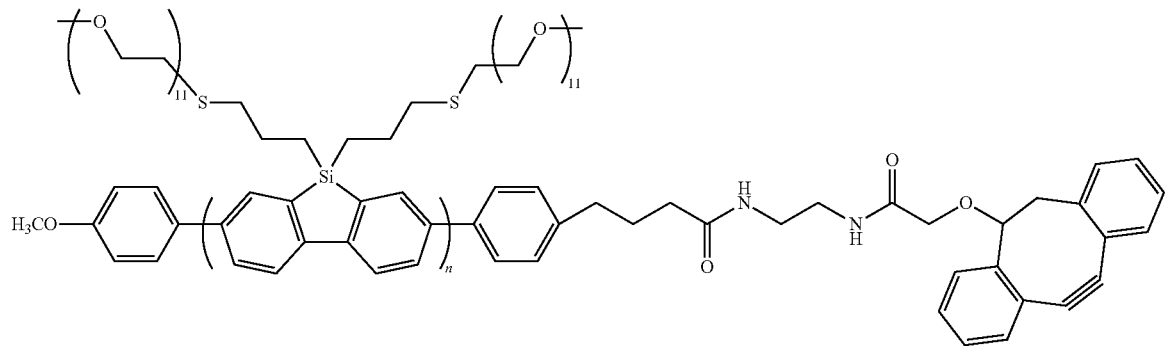

N-(2-aminoethyl)-2-(5,6-dihydro-11,12-didehydro-dibenzo[a,e]cycloocten-5-yloxy)acetamide (DIBO-amine, 3 mg, 0.0075 mmol) and polymer-capped with TFP ester (16) (10 mg, 0.0075 mmol) were dissolved in a dry 3-mL vial in 0.3 mL anhydrous DMF. 0.1 mL of N,N-diisopropylethylamine was added to the mixture, and the reaction was stirred vigorously overnight at room temperature. The solution was evaporated to dryness and then dissolved in 2 mL DI water. The aqueous solution was filtered through 0.45 μm glass fiber filter and then centrifuged at 12,000× for 10 min. The supernatant was collected and washed 6 times with ethyl acetate. The solution then was filtered 3 times through Amicon® Ultra-4 Centrifugal Filter Units (MWCO, 10K) to remove excess reagents. The polymer product (17) was dried in vacuum and collected as amber wax (6.5 mg; yield: 65%).

Example 18

Azide Derivative of Poly(2,7-dibenzosilole)-PEG11 Analogue (18)

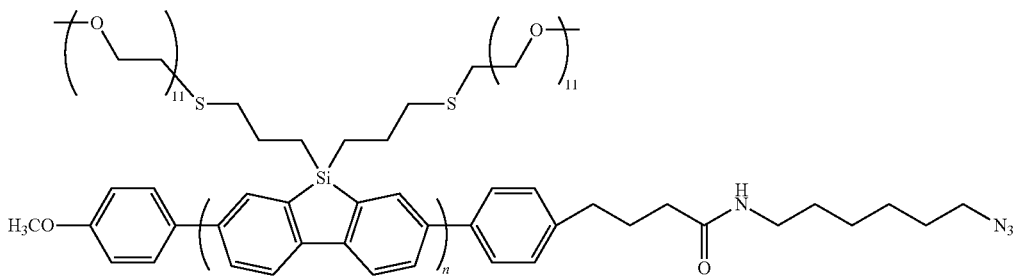

6-amino-hexanyl-1-azide, trifluoroacetic acid salt (2 mg, 0.005 mmol) and polymer-capped with TFP ester (16) (7 mg, 0.005 mmol) were dissolved in a dry 3-mL vial in 0.25 mL anhydrous DMF. 0.05 mL of N,N-diisopropylethylamine was added to the mixture, and the reaction was stirred vigorously at room temperature for overnight. The reaction mixture was processed as described in Example 16 to isolate polymer product (18) as amber wax (5.2 mg; yield: 74%).

Example 19

PEG8-TFP Ester Derivative of Poly(2,7-dibenzosilole)-PEG11 Analogue

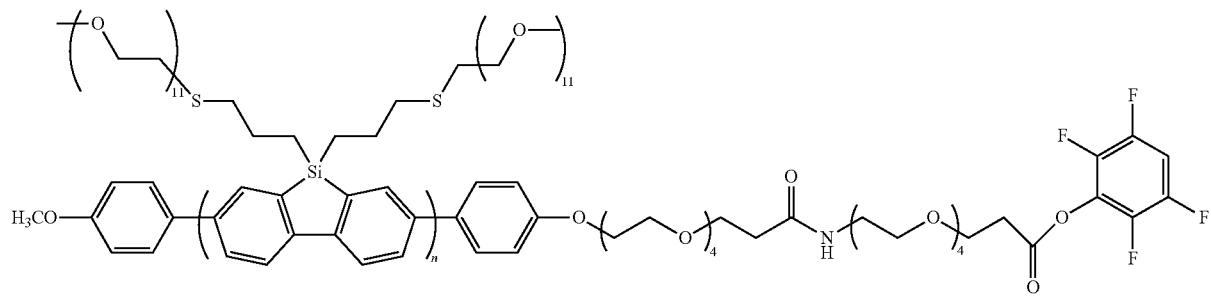

(19)

2,3,5,6-tetrafluorophenyl 2,2,2-trifluoroacetate (0.05 mL) and polymer-capped with PEG8-COOH (15) (23 mg, 0.017 mmol) obtained in Example 15 were dissolved in a dry 3 mL reaction vessel in 0.5 mL anhydrous pyridine. The reaction mixture was stirred vigorously at room temperature for 60 min, filtered through 0.45 μm glass fiber filter, and then poured into 10 mL hexane to precipitate the polymers. Polymers were collected by centrifugation and redissolved in chloroform. The precipitation-centrifugation-redissolution cycle was repeated one more time. The polymer was dissolved in 5 mL CHCl$_3$ and washed with 1M HCl once, followed dilute NaHCO$_3$ solution once and saturated NaCl solution once. The polymer product was dried over anhydrous MgSO$_4$ to evaporate all solvent yielding product (19) as amber wax (16 mg; 70%).

Example 20

PEG18-Azide Derivative of Poly(2,7-dibenzosilole)-PEG11 Analogue

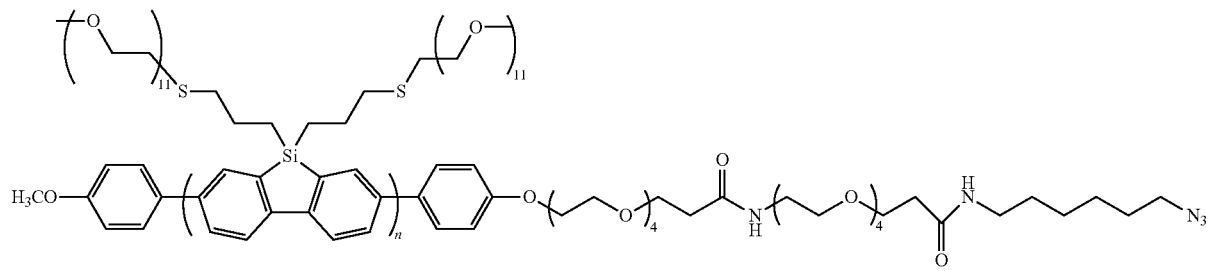

(20)

6-amino-hexanyl-1-azide, trifluoroacetic acid salt (3 mg, 0.012 mmol) and polymer-capped with PEG8-TFP ester (19) (8 mg, 0.006 mmol) were dissolved in a dry 3-mL vial in 0.25 mL anhydrous DMF. 0.05 mL of N,N-diisopropylethylamine was added to the mixture, and the reaction was stirred vigorously overnight at room temperature. The reaction mixture was processed as described in Example 17 to isolate polymer product (20) as amber wax (5.5 mg; yield: 69%).

Example 21

PEG10-Azide Derivative of Poly(2,7-dibenzosilole)-PEG11 Analogue

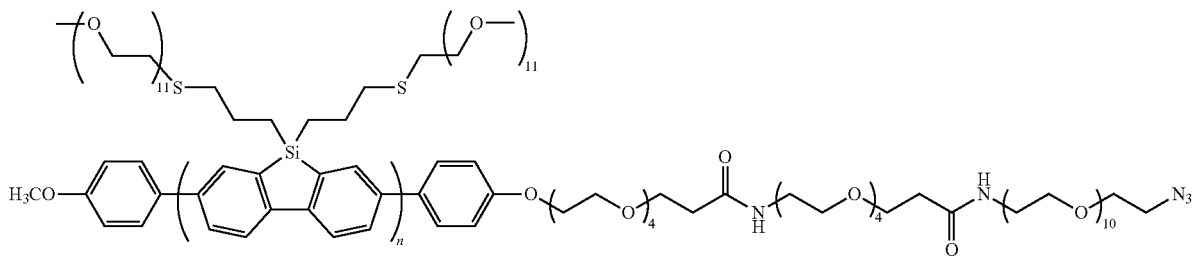

(21)

O-(2-aminoethyl)-O'-(2-azidoethyl)nonaethylene glycol (3 mg, 0.006 mmol) and polymer-capped with PEG8-TFP ester (19) (8 mg, 0.006 mmol) were dissolved in a dry 3-mL vial in 0.25 mL anhydrous DMF. 0.05 mL of N,N-diisopropylethylamine was added to the mixture, and the reaction was stirred vigorously overnight at room temperature. The reaction mixture was processed as described in Example 17 to isolate polymer product (21) as amber wax (5.9 mg; yield: 74%).

Example 22

PEG5K-Azide Derivative of Poly(2,7-dibenzosilole)-PEG11 Analogue

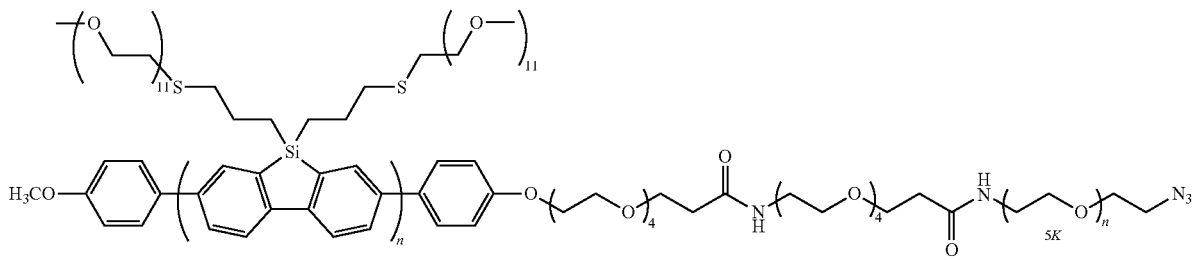

(22)

In a 10-mL dry flask, Amino-PEG5K-azide (5 mg, 0.001 mmol) and polymer-capped with PEG8-TFP ester (19) (40 mg, 0.03 mmol) were dissolved in 2 mL anhydrous DMF. 0.1 mL of N,N-Diisopropylethylamine was added to the mixture, and the reaction was stirred vigorously at room temperature for 2 days. The solution was evaporated to dryness and then dissolved in 10 mL DI water. The aqueous solution was further processed as described in Example 17 to isolate polymer product (22) as amber wax (27 mg; yield: 60%).

Example 23

Poly[(2,7-dibenzosilole)-PEG11-co-fluorene-PEG11] Copolymer

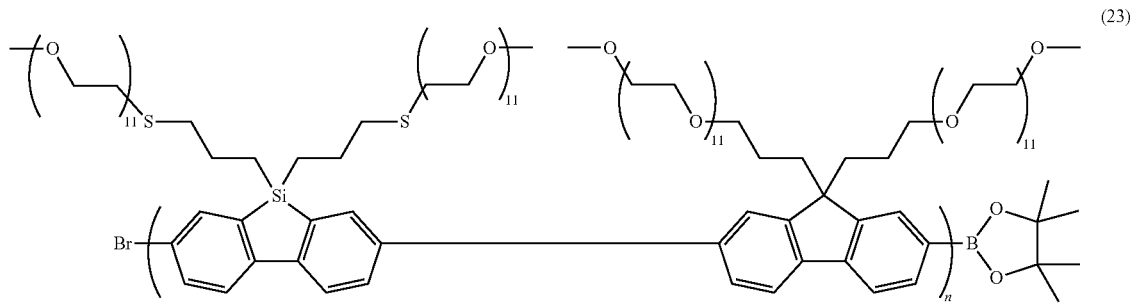

Compound (23) (n=33) was prepared in a similar method as described in Example 13, with an exception that 2,2'-(9,9-di(2,5,8,11,14,17,20,23,26,29,32,35-dodecaoxaoctatriacontan-38-yl)-9H-fluorene-2,7-diyl)bis(4,4,5,5-tetramethyl-1,3,2-dioxaborolane) instead of Compound (6) was used in polymerization reaction. Gel permeation chromatography (GPC, THF, polystyrene standard: $M_w$=55,000 g/mol, $M_n$=43,000; PDI=1.27).

Example 24

Poly[(2,7-dibenzosilole)-PEG11-co-fluorene-PEG11 (20%-co-80%)] Copolymer

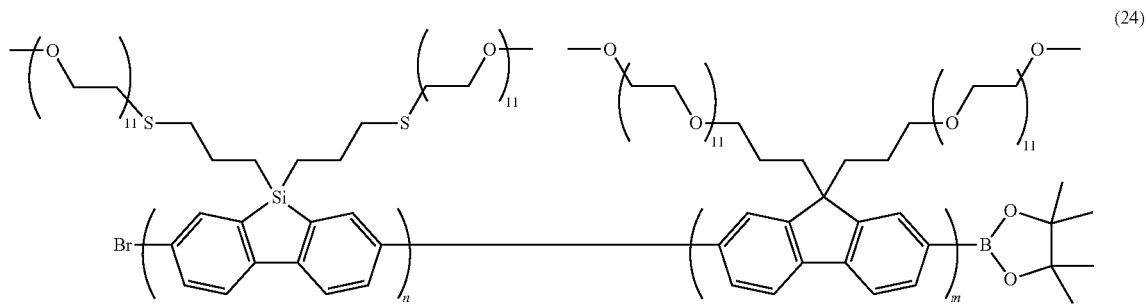

Compound (24) (m/n=4) was prepared in a similar method as described in Example 13, with an exception that 1 equivalent of 2,2'-(9,9-di(2,5,8,11,14,17,20,23,26,29,32,35-dodecaoxaoctatriacontan-38-yl)-9H-fluorene-2,7-diyl)bis(4,4,5,5-tetramethyl-1,3,2-dioxaborolane), 0.6 equivalent of 38,38'-(2,7-dibromo-9H-fluorene-9,9-diyl)bis(2,5,8,11,14,17,20,23,26,29,32,35-dodecaoxaoctatriacontane) and 0.4 equivalent of 3,7-dibromo-5,5-di(2,5,8,11,14,17,20,23,26,29,32-undecaoxa-35-thiaoctatriacontan-38-yl)-5H-dibenzo[b,d]silole (5) were used in polymerization reaction. Gel permeation chromatography (GPC, THF, polystyrene standard: $M_w$=49,000 g/mol, PDI=2.28).

Example 25

Poly[(2,7-dibenzosilole)-PEG11-co-fluorene-PEG11 (5%-co-95%)] Copolymer

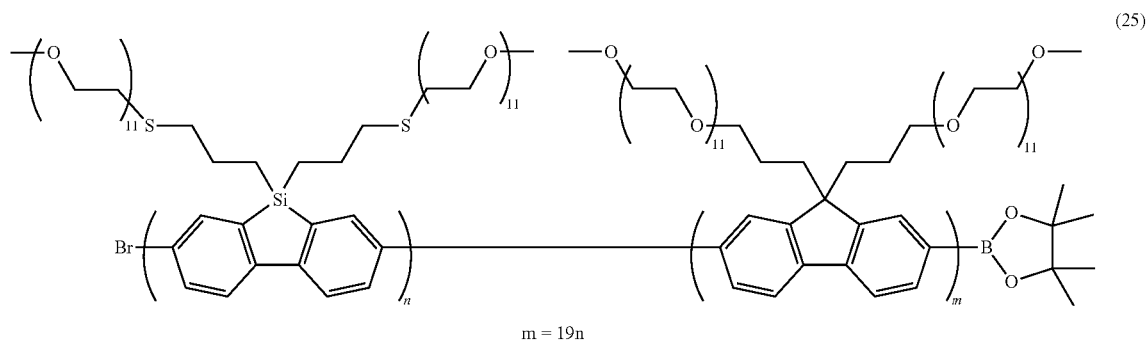

(25)

m = 19n

Figure 9:
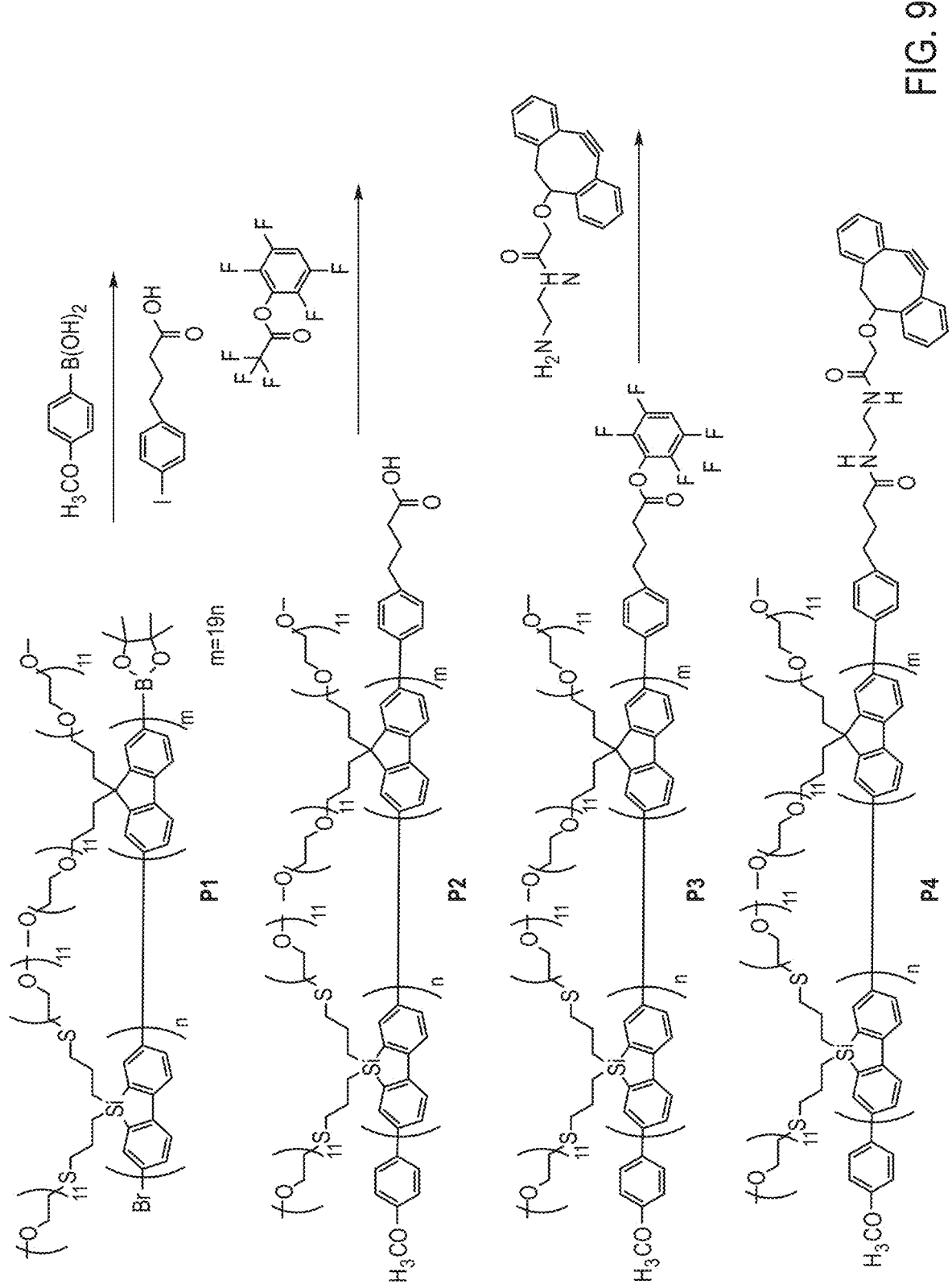
FIG. 9 is a reaction scheme for derivatizing a dibenzosilole polymer with DIBO.

Compound (25) (m/n=19) was prepared in a similar method as described in Example 13, with an exception that 1 equivalent of 2,2'-(9,9-di(2,5,8,11,14,17,20,23,26,29,32,35-dodecaoxaoctatriacontan-38-yl)-9H-fluorene-2,7-diyl)bis(4,4,5,5-tetramethyl-1,3,2-dioxaborolane), 0.9 equivalent of 38,38'-(2,7-dibromo-9H-fluorene-9,9-diyl)bis(2,5,8,11,14,17,20,23,26,29,32,35-dodecaoxaoctatriacontane) and 0.1 equivalent of 3,7-dibromo-5,5-di(2,5,8,11,14,17,20,23,26,29,32-undecaoxa-35-thiaoctatriacontan-38-yl)-5H-dibenzo[b,d]silole (5) were used in polymerization reaction. Gel permeation chromatography (GPC, THF, polystyrene standard: $M_w$=70,000 g/mol, PDI=1.4). Compound (25) was derivatized with DIBO using a method as described in Example 17 (see, FIG. 9).

Example 26

PEG8-COOH Derivative of Poly[(2,7-dibenzosilole)-PEG11-co-fluorene-PEG11 (5%-co-95%)] Copolymer

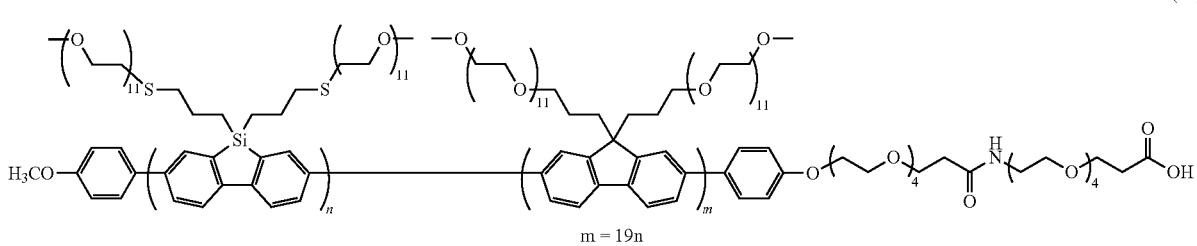

(26)

m = 19n

Compound (26) was prepared in a similar method as described in Example 15, with the exception that Compound (25) obtained in Example 25 was used for end-capping.

Example 27

Poly[(2,7-dibenzosilole)-PEG7-co-fluorene-PEG11 (5%-co-95%)] Copolymer

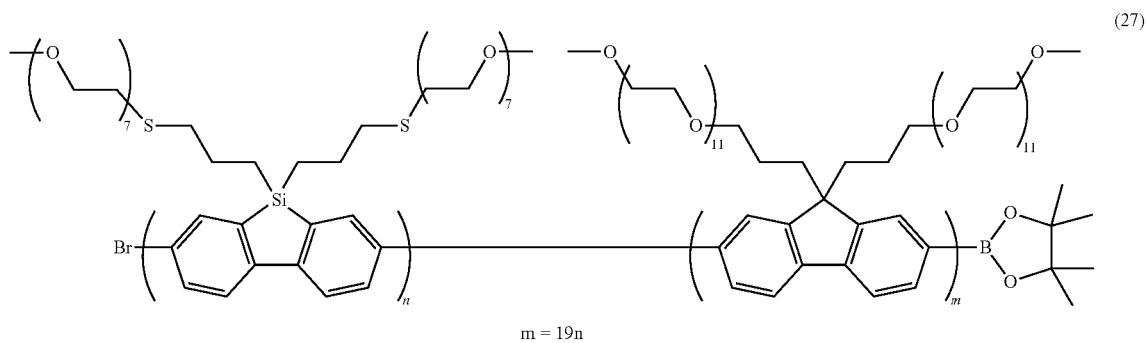

(27)

m = 19n

Compound (27) was prepared in a similar method as described in Example 13, with an exception that 1 equivalent of 2,2'-(9,9-di(2,5,8,11,14,17,20,23,26,29,32,35-dodecaoxaoctatriacontan-38-yl)-9H-fluorene-2,7-diyl)bis(4,4,5,5-tetramethyl-1,3,2-dioxaborolane), 0.9 equivalent of 38,38'-(2,7-dibromo-9H-fluorene-9,9-diyl)bis(2,5,8,11,14,17,20,23,26,29,32,35-dodecaoxaoctatriacontane) and 0.1 equivalent of 3,7-dibromo-5,5-di(2,5,8,11,14,17,20-heptaoxa-23-thiahexacosan-26-yl)-5H-dibenzo[b,d]silole (5) were used in polymerization reaction. Gel permeation chromatography (GPC, THF, polystyrene standard: $M_w$=37,000 g/mol, PDI=1.95).

Example 28

PEG4-COOH Derivative of Poly[(2,7-dibenzosilole)-PEG7-co-fluorene-PEG11 (5%-co-95%)] Copolymer

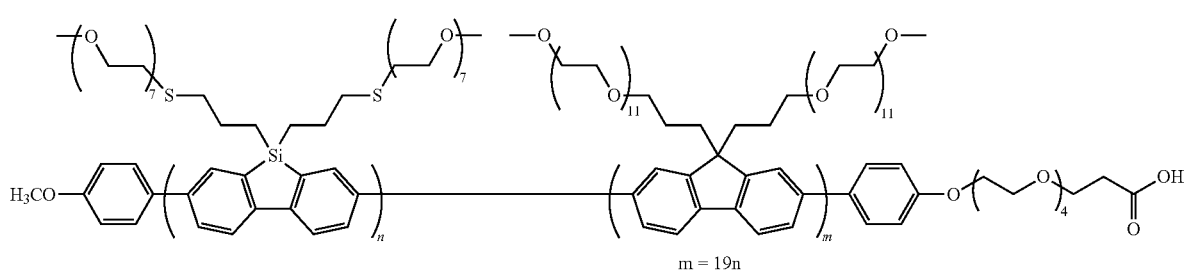

(28)

m = 19n

Compound (28) was prepared in a similar method as described in Example 14, with exception of Compound (27) obtained in Example 27 and 1-(4-bromophenoxy)-3,6,9,12-tetraoxapentadecan-15-oic acid (10) were used for end-capping.

Example 29

PEG4-Succinimidyl (NHS) Ester Derivative of Poly [(2,7-dibenzosilole)-PEG7-co-fluorene-PEG11 (5%-co-95%)] Copolymer

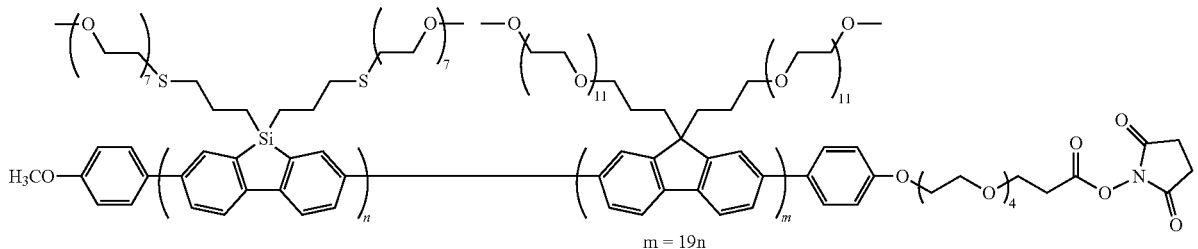

(29)

m = 19n

In a 3 mL amber vial, the polymer (28) obtained in Example 28 (15 mg) was dissolved in 0.5 mL anhydrous THF and 0.1 mL of extra dry pyridine was added. And then 2,5-dioxopyrrolidin-1-yl 2,2,2-trifluoroacetate (30 mg, 0.14 mmol) was added to the mixture and the reaction was stirred at room temperature for 1 hour. The reaction was evaporated to dryness using rotary evaporator. The crude product was dissolved in 70% EtOH/30% $H_2O$, and then filtered through 0.45 μm glass fiber filter. The solution was then transferred into Amicon Ultra Centrifugal Filter (30K MWCO), and spun for 30 min for removing excessive reagents. The polymer product (29) was dried in vacuum and collected as amber oil (11 mg; yield: 73%). The terminal succinimidyl (NHS) ester group on compound (29) can serve a site for attachment of a substance bearing an amine group (e.g., a protein, nucleic acid, dye, or solid support).

Example 30

Measurement of Optical Properties

Figure 6A:
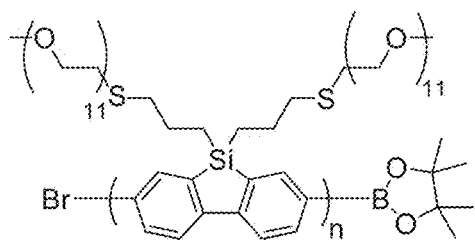
FIG. 6A shows the chemical structure for Compound 13.
Figure 6B:
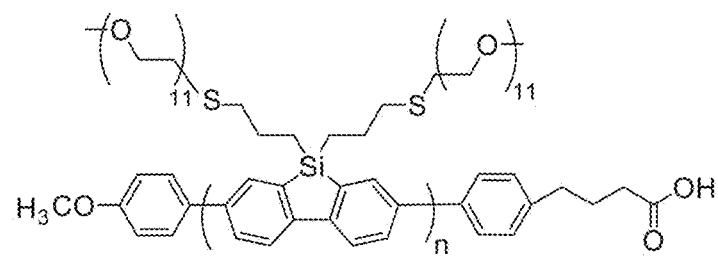
FIG. 6B shows the chemical structure for Compound 14.
Figure 6C:
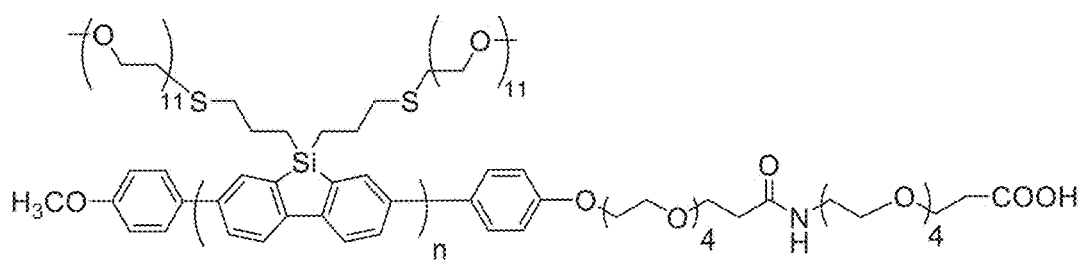
FIG. 6C shows the chemical structure for Compound 15.
Figure 6D:
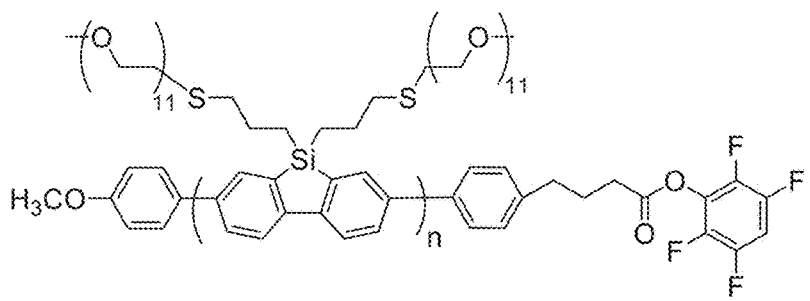
FIG. 6D shows the chemical structure for Compound 16.
Figure 6E:
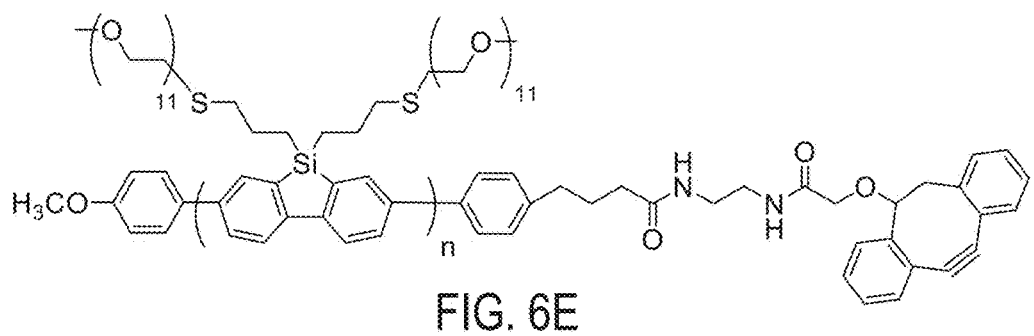
FIG. 6E shows the chemical structure for Compound 17.
Figure 6F:
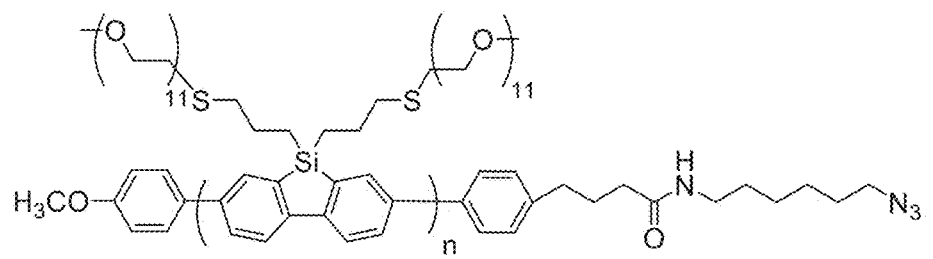
FIG. 6F shows the chemical structure for Compound 18.
Figure 6G:
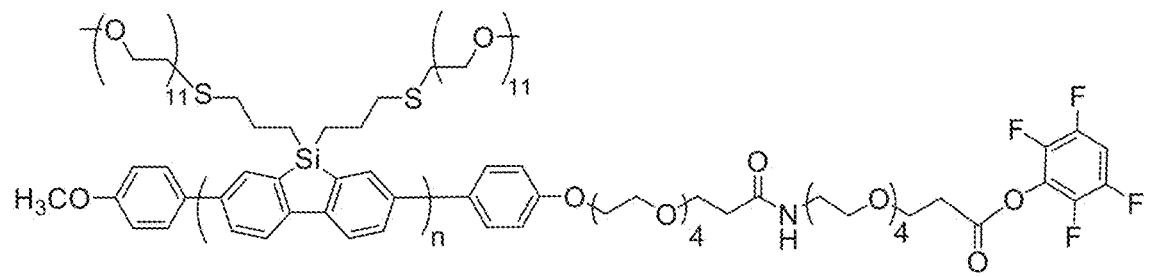
FIG. 6G shows the chemical structure for Compound 19.
Figure 6H:
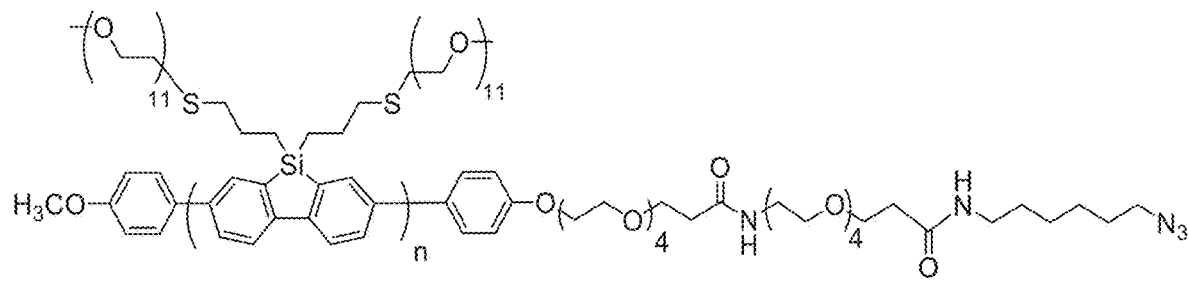
FIG. 6H shows the chemical structure for Compound 20.
Figure 6I:
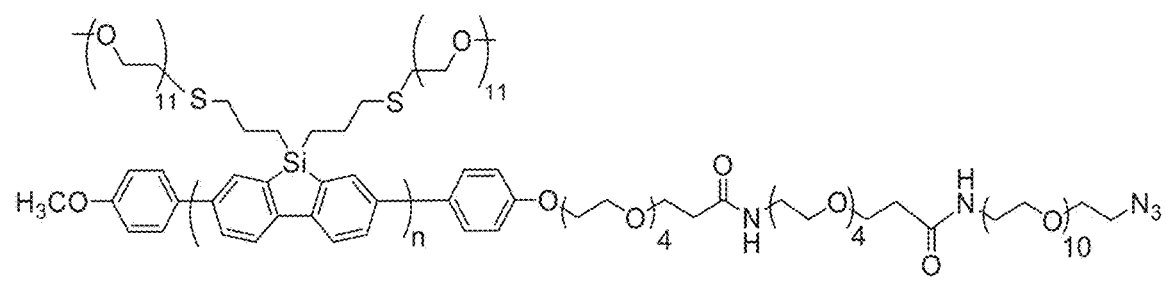
FIG. 6I shows the chemical structure for Compound 21.
Figure 6J:
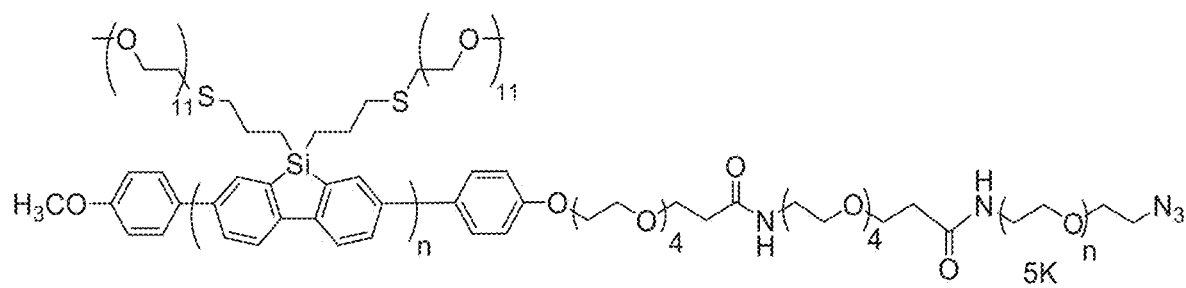
FIG. 6J shows the chemical structure for Compound 22.
Figure 6K:
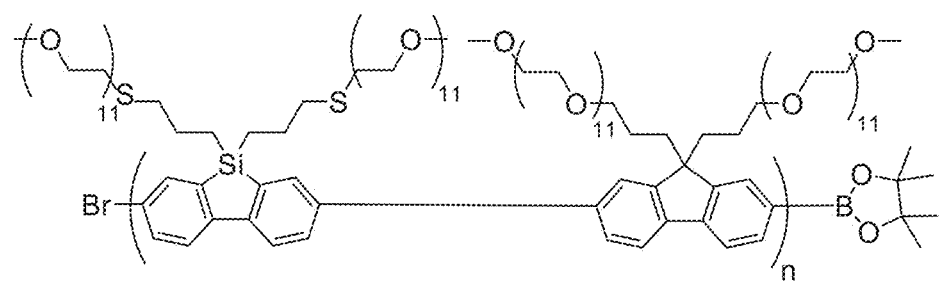
FIG. 6K shows the chemical structure for Compound 23.
Figure 6L:
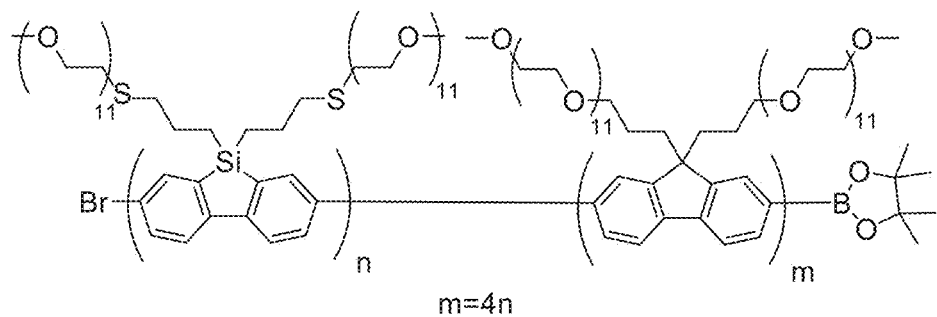
FIG. 6L shows the chemical structure for Compound 24.
Figure 6M:
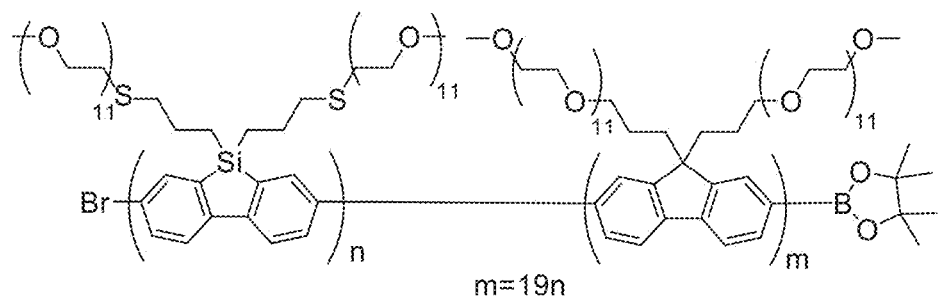
FIG. 6M shows the chemical structure for Compound 25.
Figure 6N:
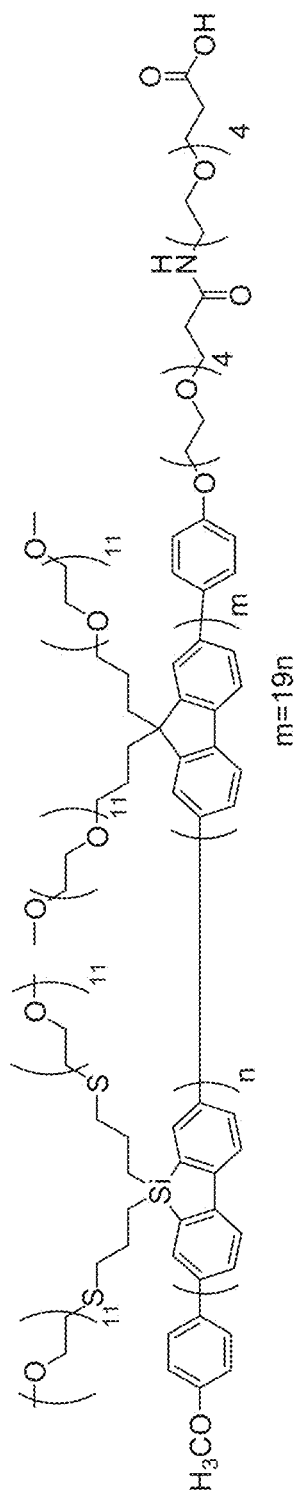
FIG. 6N shows the chemical structure for Compound 26.
Figure 6O:
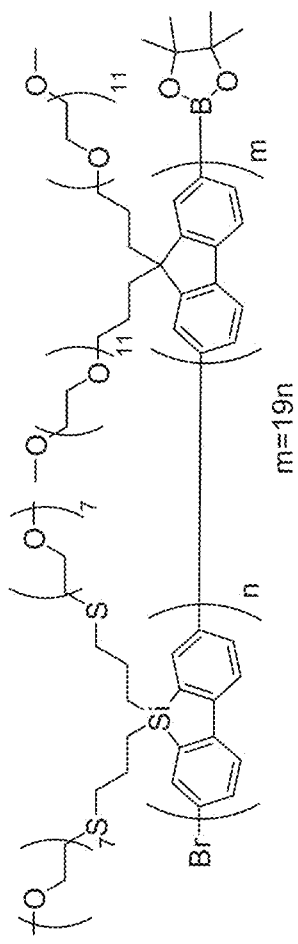
FIG. 6O shows the chemical structure for Compound 27.
Figure 6P:
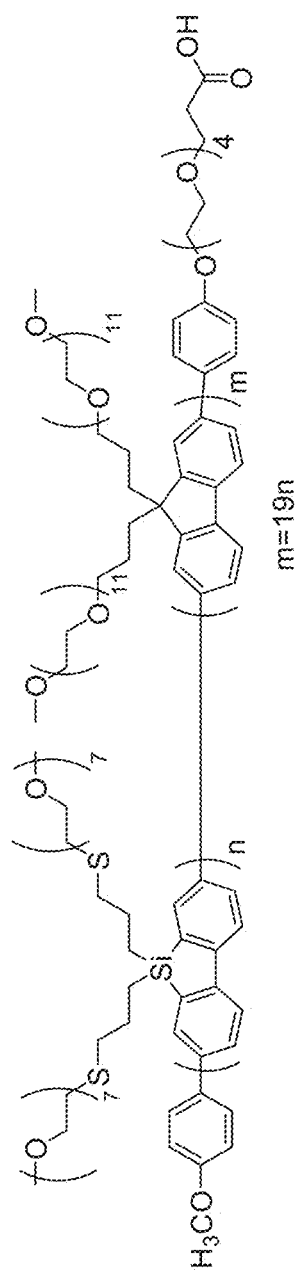
FIG. 6P shows the chemical structure for Compound 28.
Figure 6Q:
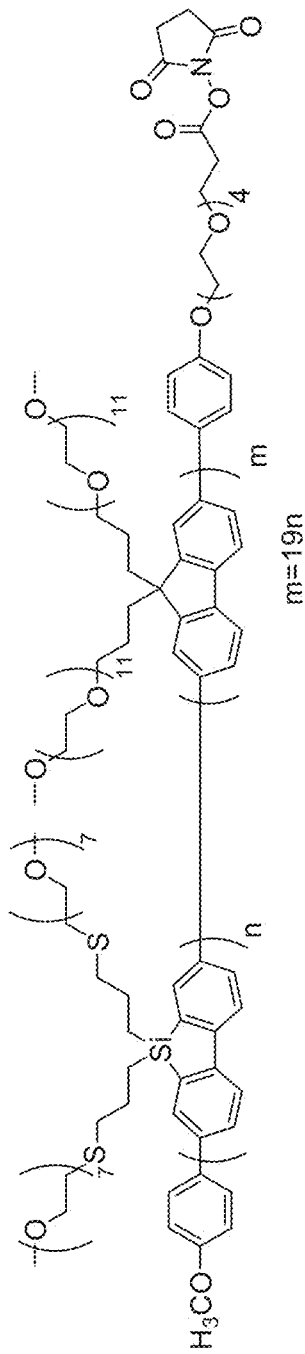
FIG. 6Q shows the chemical structure for Compound 29.

The spectral properties were evaluated for Pacific Blue™ and Alexa Fluor® 405 (Life Technologies Corporation) and the conjugated polymers (Compounds 13-29) represented by the structures shown in FIG. 6A-6Q. The absorbance wavelength maximum, ($\lambda_{ab}$), emission wavelength maximum ($\lambda_{em}$), quantum yield (QY) and extinction coefficient for each compound are presented in the table shown in FIG. 10. Fluorescence spectra were collected in aqueous solution using an excitation wavelength of 390 nm. Quantum yield was measured on a Hamamatsu absolute PL quantum yields measurement system with excitation at 390 nm. Fluorescence UV-Vis absorption and emission spectra were recorded on a Perkin-Elmer Lambda 45 UV/Vis spectrophotometer in aqueous solutions at room temperature.

The spectral characteristics of dibenzosilole-containing polymers were similar to those of poly(fluorene). The absorption maxima were centered on the 390-405 nm range, well suitable for 405 nm laser excitation typically found on flow cytometers. It is noteworthy that the introduction of dibenzosilole units into poly(fluorene) resulted in a modest (e.g., 5-10 nm) blue-shift in absorption maxima, corresponding to a relatively larger π-π* transition energy. In contrast, the fluorescent emission peaks were red-shifted and broadened with increasing dibenzosilole content in the polymer backbone. The quantitative brightness measurements also illustrated the extraordinary light-emitting capability of the dibenzosilole polymers provided herein. For example, Compound 26 exhibited a maximum molar extinction coefficient of over 2 million $M^{-1}$ $cm^{-1}$ and a fluorescence quantum yield of 67%, resulting in an overall brightness substantially higher than observed with poly(fluorene) and other previously described fluorophores.

Example 31

Cellular Analysis by Flow Cytometry

Figure 2:
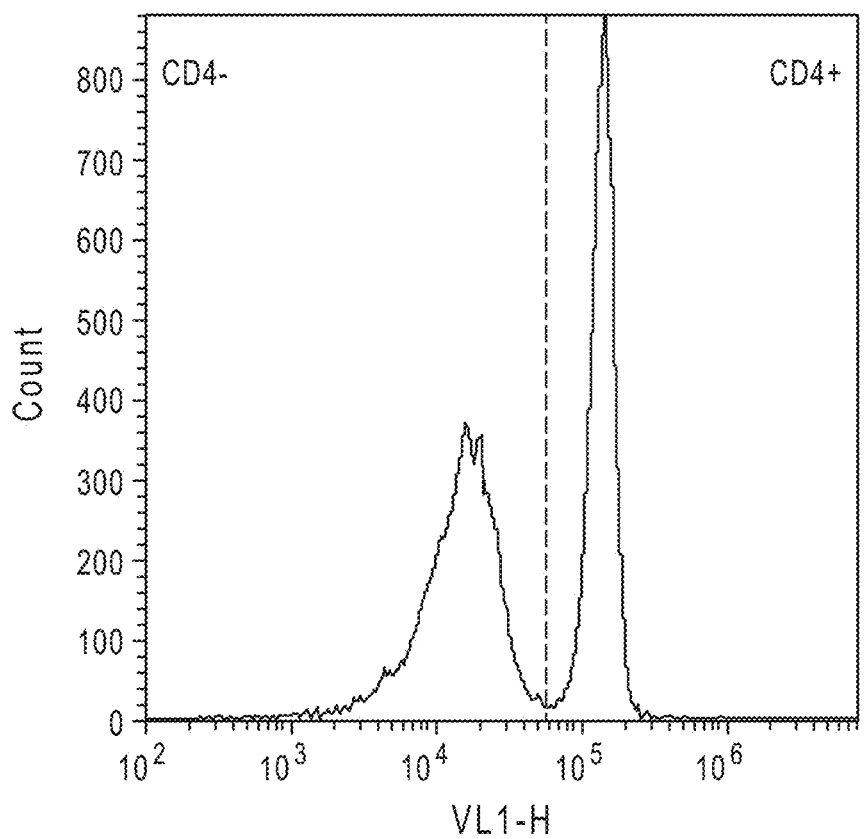
FIG. 2 is histogram calculated from the data presented in FIG. 1.

A method for detection of cells labeled with dibenzosilole polymers using flow cytommetry is described. The method was used to evaluate the performance of polymer candidates as described herein. Polymer candidates were conjugated to a mouse monoclonal antibody against human CD4 (e.g., anti-human CD4 antibody; Life Technologies Corporation). White blood cells were prepared from lysed whole blood. Polymer-antibody conjugates (Example 32) (125 ng) were diluted in 1% BSA in PBS, pH 7.4, and 10 μL of the conjugate solutions were added to 90 μL of $1\times10^6$ cells. Conjugates and cells were incubated for 20 minutes at room temperature. The cells then were washed 2 times with 1% BSA in PBS, pH 7.4. After the final wash, the cells were resuspended in 500 μL of 1% BSA in PBS, pH 7.4. Stained cells were analysed using the Attune® Acoustic Cytometer (Life Technologies Corporation) equipped with a 405 nm violet laser using a standard 440/50 emission filter setting. For CD4-specific staining, 10,000 lymphocyte events were collected (FIG. 1), and data were represented as a histogram (FIG. 2). Unstained cells were used as a reference. Bi-markers or histogram markers were inserted to help determine the percentage of CD4-positive cells in the lymphocyte population. The percentage of CD4-positive cells determined by the polymer-conjugated anti-CD4 antibody was compared with a known reference (i.e., RPE-CD4 conjugate). The comparative result was used to determine if the fluorochrome or conjugation methodology had an effect on the antibody performance. In addition, values from the mean fluorescence intensities of both the negative and positive peaks, as well as the standard deviation of the negative peak were used to determine the staining index of the conjugate tested. Comparison of the staining indices aided in evaluating the performance of different conjugates. Modifications to the core polymer resulting in conjugates producing a higher staining index number than the base polymer were incorporated into the next round of polymer-conjugate synthesis.

Example 32

Conjugation of Polymer Dyes to Antibodies

A method for conjugation of antibodies to DIBO-derivatized dibenzosilole-containing polymers is described. A mouse monoclonal antibody against human CD4 was modified with a water-soluble amine-reactive ester of an alkyl azide (azido (PEO)$_4$ propionic acid, succinimidyl ester, Life Technologies Corporation) at a molar ratio of 20:1. Antibody was brought to 1.25 mg/mL in sodium azide free PBS, pH 7.4. Sodium bicarbonate (1.0 M), pH 9.0, was added to a final concentration of 100 mM. Lysines on the antibody were modified by adding 1.1 mM azido (PEO)$_4$ propionic acid, succinimidyl ester in DMSO to a final concentration of 130 µM. After incubation for 20 h at 25° C., excess azido (PEO)$_4$ propionic acid, succinimidyl ester was removed with centrifugal filters with 50K MW cut-off, washing 4× with PBS, pH 7.4. Azide-modified antibody from the retentate was purified with 2-mL disposable spin columns using P-30 Gel (medium) in PBS. The product with a degree of substitution of ~5 azide moieties per antibody was used at 0.5 mg/mL in PBS for modification with DIBO-terminated dibenzosilole-containing polymer candidates at 100 µM final concentration for 72 hours at 25° C. These antibody-polymer conjugates were evaluated by flow cytometry on human lymphocytes.

Example 33

Analysis of Antibody-Polymer Conjugate by SDS-PAGE

Figure 3:
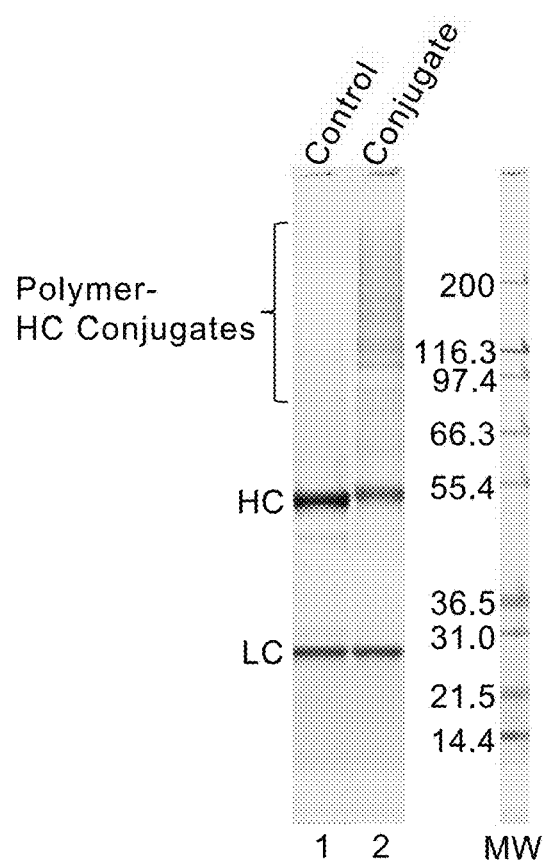
FIG. 3 is a PAGE image of azide modified fluorescent polymer added to antibody against human CD4 without DIBO-tag (negative control, lane 1) and with DIBO tag (conjugate, lane 2).
Figure 4:
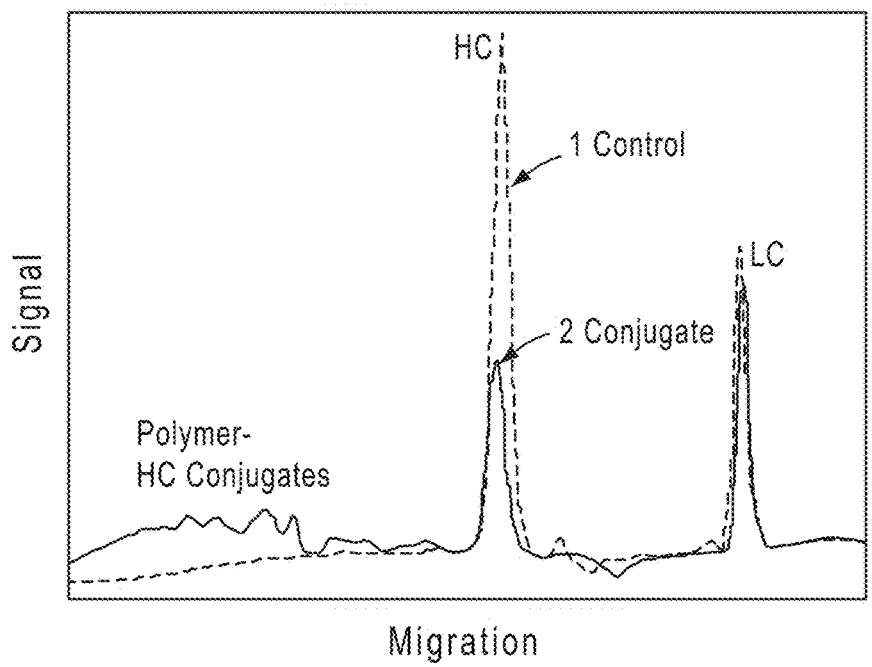
FIG. 4 is a plot showing densitometric data for samples described in Example 33.

Antibody-polymer conjugates were analyzed using NuPAGE® Novex® 4-12% Bis-Tris Gels (Life Technologies Corporation) in MOPS running buffer. 1 µg antibody was applied per lane. After staining with SYPRO® Ruby Protein Stain (Life Technologies Corporation), the gels were imaged with an FLA-9000 image scanner with an excitation of 473 nm and a 575LP filter (available from Fujifilm Life Science). FIG. 3 shows a PAGE image for azide-modified polymer (22) upon addition to antibody against human CD4 without DIBO-tag (control, lane 1) and to DIBO-modified antibody against human CD4 (conjugate, lane 2). Mark12™ Unstained Standard (Life Technologies Corporation) was used as the molecular weight standard (MW). The decrease of free heavy chain (HC) by conjugation to polymer-dye was 60%, as determined by densitometric quantitation (see, FIG. 4).

All of the compositions and/or methods and/or processes and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

All publications and patent applications mentioned in this specification are herein incorporated by reference to the same extent as if each individual publication or patent application was specifically and individually indicated to be incorporated by reference.

What is claimed is:

1. A method of preparing a polymer, comprising:
   a) combining a plurality of reactive monomers to form a reaction mixture, wherein a first portion of the reactive monomers bear first reactive groups and a second portion of the monomers bear second reactive groups, wherein the first and second reactive groups are different and capable of reacting with each other to form a polymer, and wherein at least one reactive monomer comprises a dibenzosilole group substituted with one or more first water-solubilizing groups, wherein the one or more first water-solubilizing groups is independently selected from the group consisting of alkylene oxide oligomers or polymers with greater than one alkylene oxide repeat unit, sulfonate, thiosulfate, boronate, ammonium, alkylammonium carboxylate and salts thereof; and
   b) subjecting the reaction mixture to conditions wherein the first and second reactive groups on the monomers react form a polymer.

2. The method of claim 1, wherein each reactive monomer comprises a dibenzosilole group substituted with one or more first water-solubilizing groups monomers, thereby forming a homopolymer having a polymer backbone comprising residues of dibenzosilole monomers.

3. The method of claim 1, further comprising combining a third portion of reactive monomers, each bearing first reactive groups, second reactive groups, or a combination thereof, with the first and second monomer portions, wherein the third monomer portion comprises an optionally substituted arene or heteroarene group, thereby forming a copolymer having a polymer backbone comprising residues of arene or heteroarene monomers and dibenzosilole monomers.

4. The method of claim 3, wherein the arene or heteroarene monomer bears a second water-solubilizing group, wherein the first and second water-solubilizing groups are the same or different.

5. A method of preparing a polymer, comprising polymerizing a plurality of first reactive monomers having a structure represented by Formula (II), wherein $X_1$ and $X_2$ represent reactive groups suitable for participating in a polymerization reaction,

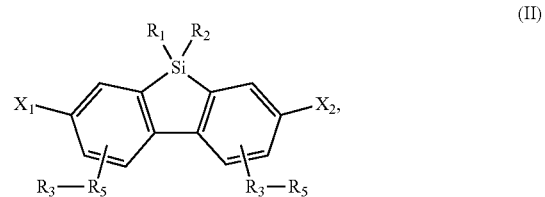

(II)

wherein, $R_1$ and $R_2$ independently are selected from the group consisting of -L-W, wherein W is a water-solubilizing group and L is an optional linker, -L-Sc—, and -L-$R_x$—, wherein Sc is a conjugated substance and $R_x$ is a first reactive group, and $R_3$, $R_4$, and $R_5$ independently are selected from the group consisting of H and optionally substituted $C_1$-$C_{20}$ alkyl, $C_{1-20}$ alkoxy, and aryl or heteroaryl groups, bromine, iodine, boron-containing groups, L-W, -L-$R_x$, and -L-Sc, provided that at least one of $R_1$-$R_5$ is or comprises a water-solublilizing group (W), wherein the one or more first water-solubilizing groups is independently selected from the group consisting of alkylene oxide oligomers or polymers with greater than one alkylene oxide repeat unit, sulfonate, thiosulfate, boronate, ammonium, alkylammonium carboxylate and salts thereof.

6. The method of claim 5, comprising polymerizing the plurality of first reactive monomers by Suzuki polymerization.

7. A method of producing a water-soluble, dibenzosilole derivative, comprising:
a) combining a compound having a structure represented by Formula (VI) and a second compound having a structure W-L-SH, wherein W is a water-solubilizing group, L is a linker, and SH is a thiol group, in a suitable solvent to form a reaction mixture; and
b) irradiating the reaction mixture with light to facilitate reaction between the first compound and the second compound, thereby producing a water-soluble compound having a structure represented by Formula (VII):

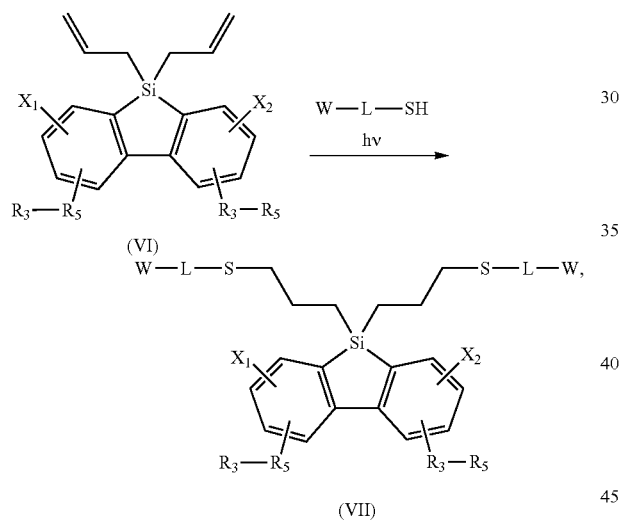

wherein $R_3$, $R_4$, and $R_5$ independently are selected from the group consisting of H and optionally substituted $C_1$-$C_{20}$ alkyl, $C_{1-20}$ alkoxy, and aryl or heteroaryl groups, fluorine, fluorine-containing groups, bromine, iodine, boron-containing groups, cyano, nitro, carboxyl, amides, ketones, phosphinoyl, phosphonates, sulfones and esters, -L-W, -L-$R_x$, and -L-Sc, and $X_1$ and $X_2$ independently are selected from the group consisting of H and optionally substituted $C_1$-$C_{20}$ alkyl, $C_{1-20}$ alkoxy, and aryl or heteroaryl groups, -L-W, -L-$R_y$, and -L-Sc, wherein $R_y$ is a second reactive group that is the same or different from R.

8. The method of claim 7, comprising combining a first compound having a structure represented by Formula (VIII) or (IX) with the second compound:

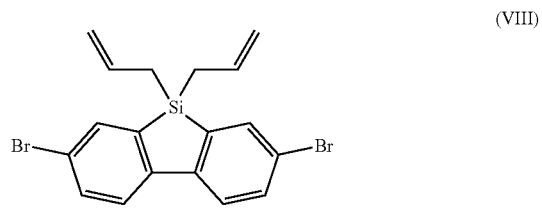

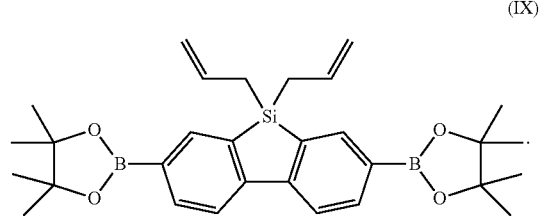

9. The method of claim 1, 5 or 7, wherein W is an ethylene glycol oligomer or polymer.

* * * * *